United States Patent [19]

Hershberger et al.

[11] Patent Number: 4,752,574

[45] Date of Patent: Jun. 21, 1988

[54] **CHIMERIC CLONING VECTORS FOR USE IN STREPTOMYCES AND *E. COLI***

[75] Inventors: Charles L. Hershberger, New Palestine; Jeffrey L. Larson, Indianapolis, both of Ind.

[73] Assignee: Eli Lilly and Company, Indianapolis, Ind.

[21] Appl. No.: 49,040

[22] Filed: Apr. 30, 1987

Related U.S. Application Data

[63] Continuation of Ser. No. 478,133, Mar. 23, 1983, abandoned, which is a continuation-in-part of Ser. No. 368,947, Apr. 16, 1982, abandoned.

[51] Int. Cl.[4] .......................... C12Q 1/04; C12Q 1/24; C12P 21/00; C12P 19/34; C12N 15/00; C12N 1/00; C12N 1/20; C07H 21/04
[52] U.S. Cl. .......................... 435/34; 435/30; 435/68; 435/91; 435/172.1; 435/172.3; 435/243; 435/253; 435/320; 536/27; 935/29; 935/73; 935/75; 935/76; 935/84
[58] Field of Search .......................... 435/30, 34, 68, 70, 435/71, 91, 172.1, 172.3, 243, 253, 320; 536/27; 935/29, 73, 75, 76, 84

[56] References Cited

U.S. PATENT DOCUMENTS

| | | | |
|---|---|---|---|
| 4,332,898 | 6/1982 | Reusser et al. | 435/253 |
| 4,332,900 | 6/1982 | Manis et al. | 435/317 |
| 4,338,400 | 7/1982 | Manis et al. | 435/317 |
| 4,340,674 | 7/1982 | Manis et al. | 435/317 |
| 4,343,906 | 8/1982 | Reusser et al. | 435/172.3 |
| 4,360,597 | 11/1982 | Bibb et al. | 435/317 |
| 4,362,816 | 12/1982 | Reusser | 435/253 |
| 4,362,817 | 12/1982 | Reusser | 435/172.3 |
| 4,393,137 | 7/1983 | Manis et al. | 435/172.3 |
| 4,401,761 | 8/1983 | Manis et al. | 435/68 |
| 4,416,994 | 11/1983 | Nakatsukasa et al. | 435/70 |

FOREIGN PATENT DOCUMENTS

2048894 12/1980 United Kingdom ............. 435/172.3

OTHER PUBLICATIONS

Thompson et al: Nature 286, 525 (1980).
Bolivar: in *Genetic Engineering,* Boyer et al (ed.), Elsevier/North-Holland, 1978, pp. 59–63.
New England Biolabs Catalog (1979) pp. 11 and 33.
Toyama et al., 1980, *Plasmid* 5:306.
Suarez and Chater, 1980, *Nature* 286:527.
Bibb et al., 1977 *J. Mol. Gen. Genet.,* 154:155.
Bibb and Hopwood, 1978, *Microbiology* 1978:139.
Bibb et al., 1980, *Developments in Industrial Microbiology* 21:55.
Bibb et al., 1980, *Nature* 284:526.
Schottel et al., 1981, *J. of Bacteriology* 146(1): 360.

*Primary Examiner*—James Martinell
*Attorney, Agent, or Firm*—Mark R. Daniel; Leroy Whitaker

[57] ABSTRACT

The present invention discloses chimeric plasmid SCP2 and SCP2* cloning vectors that are useful in Streptomyces and *E. coli.* The invention further discloses transformants and a method for detecting transformants of the aforementioned vectors.

63 Claims, 5 Drawing Sheets

Restriction Site Map of Plasmids SCP2 and SCP2*

SCP2 and SCP2*

Restriction Site Map of Plasmids pJL120 and pJL121

1. pJL 120
2. pJL 121

Restriction Site Map of Plasmids pJL180 and pJL181 pJL 180 pJL 181

Restriction Site Map of Plasmids pJL 125 and pJL 190

Restriction Site Map of Plasmids pJL 195 and pJL 114 pJL 195 pJL 114

CHIMERIC CLONING VECTORS FOR USE IN STREPTOMYCES AND E. COLI

CROSS REFERENCE

This application is a continuation of application Ser. No. 478,133, filed on Mar. 23, 1983, now abandoned, which is a continuation-in-part of application Ser. No. 368,947, filed on Apr. 16, 1982, now abandoned.

SUMMARY OF THE INVENTION

The present invention comprises selectable novel recombinant DNA cloning vectors comprising a functional origin of replication-containing restriction fragment of plasmid SCP2 or SCP2* and a functional origin of replication-containing and antibiotic resistance-conferring restriction fragment of a plasmid that is functional in E. coli. The invention further comprises transformants and a method for detecting transformants of the aforementioned vectors.

The present invention provides selectable cloning vectors for use in Streptomyces and E. coli. Heretofore, the development and exploitation of recombinant DNA technology in Streptomyces have been retarded and made especially difficult because of the general lack of selectable cloning vectors. The vectors of the present invention are functional and selectable in both Streptomyces and E. coli and therefore represent a significant advance in the technical art.

The present vectors are particularly useful because they are small, versatile, and can be transformed and selected in Streptomyces or E. coli. Since over half of the clinically important antibiotics are produced by Streptomyces strains, it is desirable to develop cloning systems and vectors that are applicable to that industrially important group. The present invention provides such vectors and thus allows for the cloning of genes into Streptomyces both for increasing the yields of known antibiotics as well as for the production of new antibiotics and antibiotic derivatives.

The present invention provides vehicles for cloning DNA into Streptomyces host cells and also allows for the convenient selection of transformants. Since transformation is a very low frequency event, such a functional test is a practical necessity for determining which cell(s), of among the millions of cells, has acquired the plasmid DNA. This is important because DNA sequences that are non-selectable can be inserted into the vectors and, upon transformation, cells containing the vector and the particular DNA sequence of interest can be isolated by appropriate phenotypic selection.

For purposes of the present invention as disclosed and claimed herein, the following terms are as defined below.

Recombinant DNA Cloning Vector—any autonomously replicating agent, including but not limited to plasmids, comprising a DNA molecule to which one or more additional DNA segments can or have been added.

Transformation—the introduction of DNA into a recipient host cell that changes the genotype and consequently results in a change in the recipient cell.

Transformant—a recipient host cell that has undergone transformation.

E. coli Origin of Replication—a DNA sequence that controls and allows for replication of a plasmid or other vector in E. coli.

Sensitive Host Cell—a host cell that cannot grow in the presence of a given antibiotic without a DNA segment that confers resistance thereto.

Restriction Fragment—any linear portion or whole of plasmid or chromosomal DNA generated by the action of one or more restriction enzymes.

Plasmid pLR1 or pLR4 3.4kb BamHI Restriction Fragment—the same 3.4kb BamHI neomycin resistance-conferring fragment contained in plasmid pIJ2.

$Amp^R$—the ampicillin resistant phenotype.
$Amp^S$—the ampicillin sensitive phenotype.
$Tet^R$—the tetracycline resistant phenotype.
$Tet^S$—the tetracycline sensitive phenotype.
$CM^R$—the chloramphenicol resistant phenotype.
$CM^S$—the chloramphenicol sensitive phenotype.
$Neo^R$—the neomycin resistant phenotype.
$Neo^S$—the neomycin sensitive phenotype.
$Thio^R$—the thiostrepton resistant phenotype.
$Thio^S$—the thiostrepton sensitive phenotype.

$Neo^R$, $Neo^S$, $Thio^R$, and $Thio^S$ refer only to results of tests in Streptomyces as used in this disclosure. $Amp^R$, $Amp^S$, $Tet^R$, $Tet^S$, $Cm^R$ and $Cm^S$ refer only to results of tests in E. coli as used in this disclosure.

DETAILED DESCRIPTION OF THE INVENTION

The present invention comprises recombinant DNA cloning vectors comprising:

(a) a functional origin of replication-containing restriction fragment of plasmid SCP2 or SCP2*, (b) a restriction fragment comprising an E. coli origin of replication, (c) one or more DNA segments that confer resistance to at least one antibiotic when transformed into a cell of E. coli, said cell being sensitive to the antibiotic for which resistance is conferred, and (d) one or more DNA segments that independently confer either or both of the Streptomyces tra function or resistance to at least one antibiotic when transformed into a cell of Streptomyces, said cell being sensitive to the antibiotic for which resistance is conferred.

The invention further comprises transformants and a method for detecting transformants of the aforementioned vectors.

The vectors of the present invention are best constructed by ligating an origin of replication-containing and Streptomyces tra function-conferring restriction fragment of plasmid SCP2 or SCP2* into an E. coli origin of replication-containing and antibiotic resistance-conferring restriction fragment of an E. coli plasmid. Plasmids SCP2 and SCP2*, from which origins of replication are constructed, are each ~31kb and show similar restriction patterns. Plasmid SCP2* arose as a spontaneous mutant of plasmid SCP2 and codes for a selectable colony pock morphology. Although the pock is distinguishable from that of plasmid SCP2, in other ways plasmids SCP2 and SCP2* are virtually identical.

Figure 1:
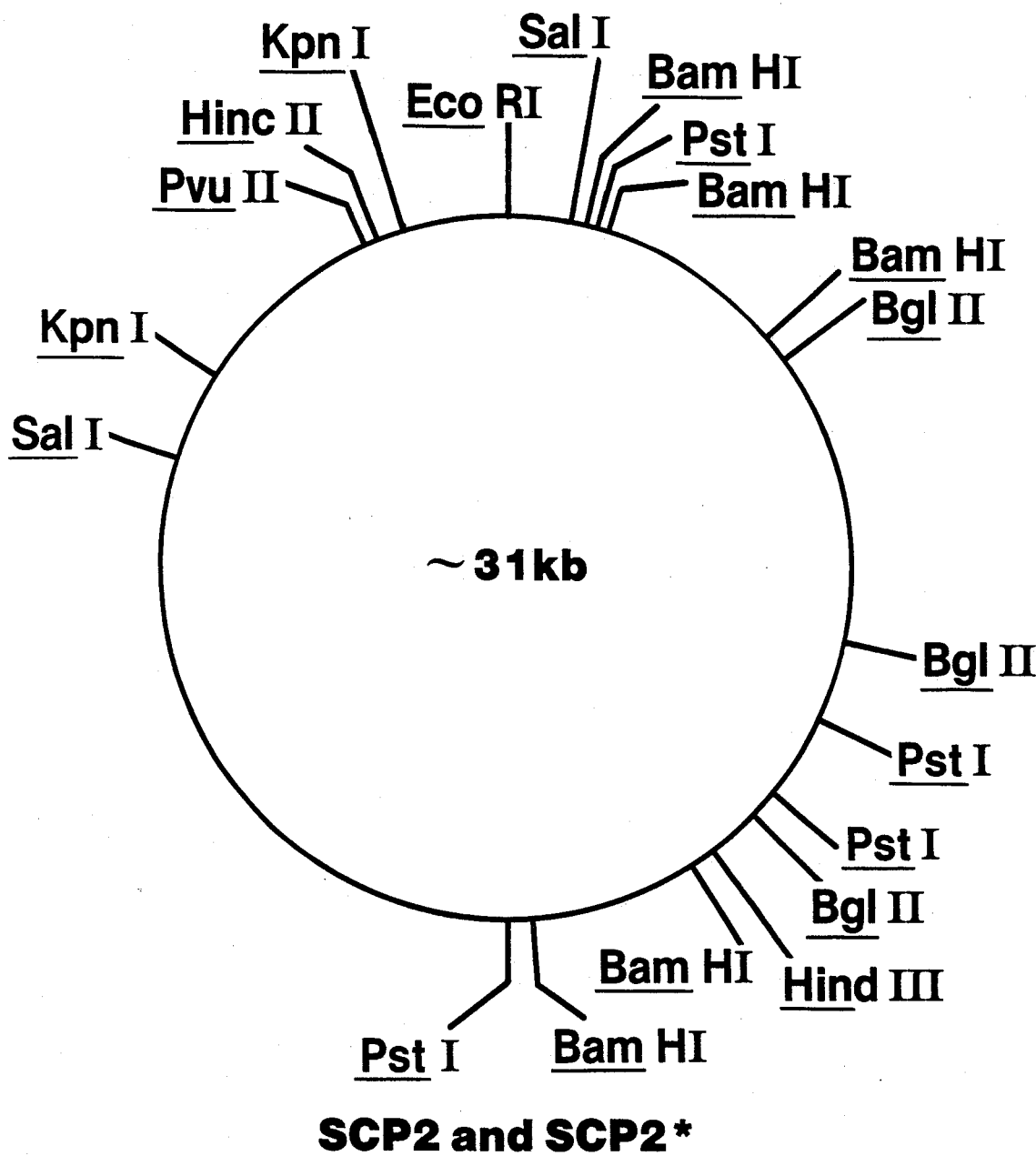
FIG. 1 shows restriction maps of SCP2 and SCP2*.

Since the present disclosure teaches that the Streptomyces tra function and the origin of replication of plasmids SCP2 and SCP2* are within their respective ~5.4kb EcoRI-SalI restriction fragments, a variety of different origin of replication-containing and Streptomyces tra function-conferring fragments can be generated. This is accomplished by digestion with restriction enzymes that cut outside the ~5.4kb EcoRI-SalI region. A detailed restriction site map of plasmid SCP2* (and thus also plasmid SCP2) is presented in FIG. 1 of the accompanying drawings.

Plasmids SCP2 and SCP2* can be conventionally isolated respectively from the Streptomyces coelicolor A3(2) and Streptomyces coelicolor M110 strains deposited and made part of the permanent stock culture collection of the Northern Regional Research Laboratory, Peoria, Ill. Streptomyces coelicolor A3(2) is available to the public as a preferred source and stock reservoir of plasmid SCP2 under the accession number 15042. Streptomyces coelicolor M110 is available to the public as a preferred source and stock reservoir of plasmid SCP2* under the accession number 15041.

Many tra function-conferring and origin of replication-containing restriction fragments of plasmids SCP2 and SCP2* can be constructed. Those specifically exemplified, for illustrative purposes, include the ~5.4kb EcoRI-SalI, the ~6.0kb SalI, the ~19kb EcoRI-HindIII, and the ~31kb EcoRI restriction fragments of plasmid SCP2* and the ~31kb BglII restriction fragment of plasmid SCP2. The aforementioned plasmid SCP2* and SCP2 fragments were respectively ligated to an origin of replication-containing and antibiotic resistance-conferring fragment of E. coli plasmids pBR325 and pBR322. Those skilled in the art will recognize that although not required, it is convenient for both the DNA segment that confers antibiotic resistance in E. coli and the E. coli origin of replication to comprise a restriction fragment of the same E. coli plasmid.

Thus, for convenience and ease of construction, the ~31kb EcoRI fragment of plasmid SCP2* and the ~6kb EcoRI fragment of plasmid pBR325 were ligated to form illustrative plasmids pJL120 and pJL121. Recombinant plasmids of two orientations result because the fragments can be ligated in either direction. Similarly, ligation of the SCP2* ~6.0kb SalI fragment and the ~6kb SalI fragment of pBR325 results in the illustrative plasmids pJL180 and pJL181; ligation of the SCP2* ~5.4kb EcoRI-SalI fragment and the ~4.8kb EcoRI-SalI fragment of pBR325 results in the illustrative plasmid pJL125; and ligation of the SCP2 BamHI digest and the ~4.4kb BamHI fragment of plasmid pBR322 results in the illustrative plasmid pJL114.

All of the aforementioned vectors are readily selectable in each of E. coli and Streptomyces. For example, in E. coli, plasmids pJL120 and pJL121 confer ampicillin and tetracycline resistance; plasmids pJL180 and pJL181 confer ampicillin and chloramphenicol resistance; and plasmids pJL125 and pJL114 confer only ampicillin resistance. Therefore, the vectors are conventionally selectable in the E. coli host system by adding the appropriate antibiotic to the culture medium.

The aforementioned vectors also produce the 'pock' phenotype and therefore are conventionally selectable in Streptomyces. The 'pock' phenotype is an assayable trait and known phenomenon (Bibb and Hopwood, 1981, J. Gen. Microbiol. 126:427) associated with lethal zygosis and the tra function (tra=genes coding for sexual transmissability) of Streptomyces sex factors. Three distinct 'pock' morphologies are associated with transformants, when plated on an appropriate indicator strain, of plasmids SCP2, SCP2*, and SCP2 and SCP2* derivatives. The colony morphology identified with the wild-type SCP2 and the mutant SCP2* are respectively designated herein as P and P*. A third and heretofore unknown pock morphology results from cloning into the EcoRI restriction site of SCP2 or SCP2*. Such an insertion inactivates the P gene and unexpectedly results in a morphologically distinguishable minipock phenotype, designated herein as M, when transformants are appropriately plated. "Minipock" is a pock of significantly smaller size than pocks caused by either SCP2 or SCP2*.

The present invention thus provides a novel method for detecting transformants comprising:

(1) mixing Streptomyces cells, under transforming conditions, with a recombinant DNA cloning vector, said vector comprising (a) an origin of replication and P gene-containing restriction fragment of plasmid SCP2 or SCP2*, and (b) a non-lethal DNA sequence cloned into the EcoRI restriction site of said P gene, and (2) growing said Streptomyces cells on a lawn of an indicator Streptomyces strain and selecting colonies that show the M pock phenotype.

Only transformed Streptomyces cells will show the M pock phenotype and therefore transformants can be readily identified and selected. Those skilled in the art will quickly recognize, from the above description of the present pJL vectors, that plasmids pJL120, pJL121, and pJL125 code for M phenotype, that plasmids pJL180 and pJL181 code for P* phenotype, and that plasmid pJL114 codes for P phenotype. Appropriate indicator strains for expression of the pock phenotype are known and include the various SCP2− and SCP2*− strains as illustrated in the Examples below. The present vectors are thus selectable and extremely useful in Streptomyces.

The aforementioned plasmids can also be provided with a DNA segment that confers antibiotic resistance in Streptomyces. Such derivatives, specifically exemplified for illustrative purposes by plasmids pJL190 and pJL195, express an additional selectable phenotype. Plasmid pJL190 was constructed by ligating the neomycin resistance-conferring ~7.7kb EcoRI-HindIII fragment of plasmid pLR4 to the ~19kb EcoRI-HindIII fragment of plasmid pJL121. Plasmid pJL195 was constructed by ligating the pLR4 ~7.5kb EcoRI-partial SalI fragment to the ~5.4kb EcoRI-SalI fragment of plasmid pJL125. The latter pJL125 plasmid comprises the largest (5.4kb) EcoRI-SalI fragment of plasmid pSCP2* and was constructed by SalI deletion of plasmid pJL121. Illustrative plasmids pJL190 and pJL195, in addition to neomycin resistance, also express the M phenotype as discussed above.

Plasmid pLR4, the source of the neomycin resistance conferring fragments, is ~7.7kb and is constructed by ligating BamHI-treated plasmids pBR322 and pLR1. Plasmid pLR1 is 14.8kb and is constructed by ligating HindIII-treated plasmid pIJ2, disclosed in Thompson et al., 1980, Nature 286:525, to HindIII-treated plasmid pBR322. As is readily apparent to those skilled in the art, both plasmids pLR4 and pLR1 contain the same neomycin resistance gene and thus either plasmid can be used for constructing the aforementioned pJL neomycin resistant vectors.

An additional neomycin resistance-conferring plasmid, designated as pJL192, was isolated as a spontaneous mutant of plasmid pJL190 resident in Streptomyces griseofuscus. Plasmid pJL192 specifies resistance to elevated levels of neomycin and therefore comprises a novel neomycin resistance gene which is distinguishable from the resistance gene comprising plasmids pJL190, pJL195, pIJ2, pLR4, and pLR1. In a similar manner, an additional neomycin resistance-conferring plasmid, designated as pJL199, was isolated as a spontaneous mutant of plasmid pJL195. Those skilled in the art will recognize that the novel neomycin resistance gene of plasmid pJL192 or pJL199 can be readily excised and ligated to other vectors. The gene allows for improved and more efficient selection of transformants. As in the case of plasmids pJL190 and pJL195, transformants of plasmids pJL192 and pJL199 express the M phenotype when plated on an appropriate indicator strain.

Plasmid pJL192 can be conventionally isolated from $E.$ $coli$ K12 C600R$_k$-M$_k$-/pJL192, a strain deposited and made part of the permanent stock culture collection of the Northern Regional Research Laboratory, Peoria, Illinois. It is available to the public as a stock reservoir and preferred source of plasmid pJL192 under the accession number B-15040.

A DNA segment that confers resistance to antibiotic thiostrepton, exemplified by the ~1.35kb BamHI restriction fragment of plasmid pLR2, can also be used with or substituted for the neomycin resistance-conferring segment. Plasmid pLR2, the source of the thiostrepton resistance conferring fragment, is ~18.7kb and is constructed by ligating HindIII treated plasmid pIJ6, disclosed in Thompson et al., 1980, Nature 286:525, to HindIII treated plasmid pBR322. Plasmid pLR2 is functional in $E.$ $coli$ and therefore can be amplified and isolated conveniently for subsequent manipulation.

For convenience and ease of construction, the thiostrepton resistance conferring ~1.35kb BamHI fragment of plasmid pLR2 was ligated into the BamHI restriction site of plasmid pBR328 to form plasmid pJL193. The ~1 kb BclI restriction fragment of pJL193 contains the thiostrepton resistance-conferring DNA segment. Therefore, ligation, as described in Examples 52–56, results in vectors that are within the scope the present invention.

Various plasmid SCP2 and SCP2* restriction fragments can be used for purposes of constructing the present invention provided that the origin of replication contained in their respective ~5.4kb EcoRI-SalI restriction fragments is present. Such additional plasmid SCP2 and SCP2* restriction fragments include, but are not limited to, the ~6kb SalI, ~15kb PstI, ~23kb BglII, ~15kb BamHI, ~14kb EcoRI-PstI, ~13kb EcoRI-BamHI, and ~15kb PstI-BamHI fragments. These fragments contain the Streptomyces tra function and can be ligated to a functional $E.$ $coli$ origin of replication-containing and antibiotic resistance-conferring restriction fragment of an E. coli plasmid. Such $E.$ $coli$ plasmids include, for example, plasmids pBR322, pBR324, pBR325, pBR327, pBR328 and the like. Therefore, the present invention is not limited to the use of either plasmid pBR322 or pBR325 as exemplified in several pJL constructions.

Although the neomycin and thiostrepton antibiotic resistance-conferring DNA segments exemplified herein are respectively the ~7.7kb EcoRI-HindIII and the ~7.5kb EcoRI-partial SalI fragments of plasmid pLR4 and the pLR2 ~1.35 BamHI and the pJL193 ~1kb BclI fragments, those skilled in the art can construct and use other DNA segments that also confer resistance to neomycin or thiostrepton. Other neomycin resistance-conferring DNA segments of plasmid pLR1 include, for example, the ~3.4kb BamHI restriction fragment, the ~3.5kb PstI restriction fragment, and the larger of the SstI-KpnI subfragments of the ~3.4kb BamHI restriction fragment. Other thiostrepton resistance-conferring segments include, for example, the ~13kb PstI fragment of plasmid pLR2. Still other DNA segments conferring resistance to the same or to different antibiotics such as, for example, hygromycin, viomycin, tylosin, erythromycin and the like, can also be constructed and used by those skilled in the art. In addition, various functional derivatives of the above described antibiotic resistance-conferring DNA segments can be constructed by adding, eliminating, or substituting nucleotides in accordance with the genetic code.

Ligation of the aforementioned derivatives, or any of the other antibiotic resistance-conferring DNA segments, to a vector comprising an $E$ $coli$ antibiotic resistance-conferring DNA segment, an $E.$ $coli$ origin of replication-containing restriction fragment, and also an origin of replication-containing restriction fragment of plasmids SCP2 or SCP2*, results in plasmids that are within the scope of the present invention. Therefore, an antibiotic resistance-conferring DNA segment can be used as a selectable marker in place of the Streptomyces tra function and associated pock phenotype. Thus, the present vectors are not limited to the use of tra alone or in combination with an antibiotic resistance-conferring DNA segment. In addition, a particular antibiotic resistance-conferring DNA segment is not limited to a single position on the present chimeric plasmids but can be ligated or inserted at varying sites provided that an origin of replication or other critical plasmid controlled physiological functions are not disrupted. Those skilled in the art understand or can readily determine which sites are advantageous for ligation or insertion of a particular DNA segment.

The various restriction fragments of plasmids SCP2, SCP2*, pBR325, pBR322 and the like, and also the various antibiotic resistance-conferring DNA segments comprising the present vectors, can be modified to facilitate ligation. For example, molecular linkers can be provided to some or all of the aforementioned DNA fragments. Thus, specific sites for subsequent ligation can be constructed conveniently. In addition, the origin of replication-containing restriction fragments can also be modified by adding, eliminating, or substituting certain nucleotides to alter characteristics and to provide a variety of restriction sites for ligation of DNA. Those skilled in the art understand nucleotide chemistry and the genetic code and thus which nucleotides are interchangeable and which DNA modifications are desirable for a specific purpose.

The recombinant DNA cloning vectors that contain the SCP2 or SCP2* Streptomyces tra function are self transmissable and thus readily transferred during mating between transformed and non-transformed Streptomyces taxa. This is advantageous because the present vectors therefore can be transformed not only by protoplast transformation but also by conventional genetic crosses. Consequently, the vectors are useful in Streptomyces strains which are difficult to protoplast thus greatly expanding the number of hosts in which genetic manipulation and DNA cloning can be done.

More importantly, DNA-libraries constructed in the present vectors can be conveniently and rapidly screened for interesting genes by conventional replica-plate mating procedures. Without the tra function, DNA must be isolated from each of the thousands of clones in the library and transformed into appropriate strains to identify clones that contain desirable genes. Since there are no broadly applicable phage vectors for use in Streptomyces, the present tra+ vectors fulfill the general cloning and screening role analogous to that of bacteriophage λ in replica-plate transduction for screening gene libraries in *E coli*. Desirable genes can thus be readily identified by the replica-plate mating procedure and then easily amplified by shuttling into *E. coli* as described in Example 20C below.

The vectors of the present invention are broadly applicable and are transformed into host cells of many Streptomyces taxa, particularly restrictionless strains of economically important taxa that produce antibiotics such as aminoglycoside, macrolide, β-lactam, polyether, and glycopeptide antibiotics. Such restrictionless strains are readily selected and isolated from Streptomyces taxa by conventional procedures well known in the art (Lomovskaya et al., 1980, Microbiological Reviews 44:206). Host cells of restrictionless strains lack restriction enzymes and therefore do not cut or degrade plasmid DNA upon transformation. For purposes of the present application, host cells containing restriction enzymes that do not cut any of the restriction sites of the present vectors are also considered restrictionless.

Preferred host cells of restrictionless strains of Streptomyces taxa that produce aminoglycoside antibiotics and in which the present vectors are especially useful and are transformed, include restrictionless cells of, for example: *S. kanamyceticus* (kanamycins), *S. chrestomyceticus* (aminosidine), *S. griseoflavus* (antibiotic MA 1267), *S. microsporeus* (antibiotic SF-767), *S. ribosidificus* (antibiotic SF733), *S. flavopersicus* (spectinomycin), *S. spectabilis* (actinospectacin), *S. rimosus* forma *paromomycinus* (paromomycins, catenulin), *S. fradiae* var. *italicus* (aminosidine), *S. bluensis* var. *bluensis* (bluensomycin), *S. catenulae* (catenulin), *S. olivoreticuli* var. *cellulophilus* (destomycin A), *S. tenebrarius* (tobramycin, apramycin), *S. lavendulae* (neomycin), *S. albogriseolus* (neomycins), *S. albus* var. *metamycinus* (metamycin), *S. hygroscopicus* var. *sagamiensis* (spectinomycin), *S. bikiniensis* (streptomycin), *S. griseus* (streptomycin), *S. erythrochromogenes* var. *narutoensis* (streptomycin), *S. poolensis* (streptomycin), *S. galbus* (streptomycin), *S. rameus* (streptomycin), *S. olivaceus* (streptomycin), *S. mashuensis* (streptomycin), *S. hygroscopicus* var. *limoneus* (validamycins), *S. rimofaciens* (destomycins), *S. hygroscopicus* forma *glebosus* (glebomycin), *S. fradiae* (hybrimycins neomycins), *S. eurocidicus* (antibiotic A16316-C), *S. aquacanus* (N-methyl hygromycin B), *S. crystallinus* (hygromycin A), *S. noboritoensis* (hygromycin), *S. hygroscopicus* (hygromycins), *S. atrofaciens* (hygromycin), *S. kasugaspinus* (kasugamycins), *S. kasugaensis* (kasugamycins), *S. netropsis* (antibiotic LL-AM31), *S. lividus* (lividomycins), *S. hofuensis* (seldomycin complex), and *S. canus* (ribosyl paromamine).

Preferred host cells of restrictionless strains of Streptomyces taxa that produce macrolide antibiotics and in which the present vectors are especially useful and are transformed, include restrictionless cells of, for example: *S. caelestis* (antibiotic M188), *S. platensis* (platenomycin), *S. rochei* var. *volubilis* (antibiotic T2636), *S. venezuelae* (methymycins), *S. griseofuscus* (bundlin), *S. narbonensis* (josamycin, narbomycin), *S. fungicidicus* (antibiotic NA-181), *S. griseofaciens* (antibiotic PA133A, B), *S. roseocitreus* (albocycline), *S. bruneogriseus* (albocycline), *S. roseochromogenes* (albocycline), *S. cinerochromogenes* (cineromycin B), *S. albus* (albomycetin), *S. felleus* (argomycin, picromycin), *S. rochei* (lankacidin, borrelidin), *S. violaceoniger* (lankacidin), *S. griseus* (borrelidin), *S. maizeus* (ingramycin), *S. albus* var. *coilmyceticus* (coleimycin), *S. mycarofaciens* (acetyl-leukomycin, espinomycin), *S. hygroscopicus* (turimycin, relomycin, maridomycin, tylosin, carbomycin), *S. griseospiralis* (relomycin), *S. lavendulae* (aldgamycin), *S. rimosus* (neutramycin), *S. deltae* (deltamycins), *S. fungicidicus* var. *espinomyceticus* (espinomycins), *S. furdicidicus* (mydecamycin), *S. eurocidicus* (methymycin), *S. griseolus* (griseomycin), *S. flavochromogenes* (amaromycin, shincomycins), *S. fimbriatus* (am.aromycin), *S. fasciculus* (anaromycin), *S. erythreus* (erythromycins), *S. antibioticus* (oleandomycin), *S. olivochromogenes* (oleandomycin), *S. spinichromogenes* var. *suragaoensis* (kujimycins), *S. kitasatoensis* (leucomycin), *S. narbonensis* var. *josamyceticus* (leucomycin A3, josamycin), *S. albogriseolus* (mikonomycin), *S. bikiniensis* (chalcomycin), *S. cirratus* (cirramycin), *S. djakartensis* (niddamycin), *S. eurythermus* (angolamycin), *S. fradiae* (tylosin, lactenocin, macrocin), *S. goshikiensis* (bandamycin), *S. griseoflavus* (acumycin), *S. halstedii* (carbomycin), *S. tendae* (carbomycin), *S. macrosporeus* (carbomycin), *S. thermotolerans* (carbomycin), *S. albireticuli* (carbomycin), and *S. ambofaciens* (spiramycin).

Preferred host cells of restrictionless strains of Streptomyces taxa that produce β-lactam antibiotics and in which the present vectors are especially useful and are transformed, include restrictionless cells of, for example: *S. lipmanii* (A16884, MM4550, MM13902), *S. clavuligerus* (A16886B, clavulanic acid), *S. lactamdurans* (cephamycin C), *S. griseus* (cephamycin A, B), *S. hygroscopicus* (deacetoxycephalosporin C), *S. wadayamensis* (WS-3442-D), *S. chartreusis* (SF 1623), *S. heteromorphus* and *S. panayensis* (C2081X); *S. cinnamonensis, S. fimbriatus, S. halstedii, S. rochei* and *S. viridochromogenes* (cephamycins A, B); *S. cattleya* (thienamycin); and *S. olivaceus, S. flavovirens, S. flavus, S. fulvoviridis, S. argenteolus*, and *S. sioyaensis* (MM 4550 and MM 13902).

Preferred host cells of restrictionless strains of Streptomyces taxa that produce polyether antibiotics and in which the present vectors are especially useful and are transformed, include restrictionless cells of, for example: *S. albus* (A204, A28695A and B, salinomycin), *S. hygroscopicus* (A218, emericid, DE3936), A120A, A286-95A and B, etheromycin, dianemycin), *S. griseus* (grisorixin), *S. conglobatus* (ionomycin), *S. eurocidicus* var. *asterocidicus* (laidlomycin), *S. lasaliensis* (lasalocid), *S. ribosidificus* (lonomycin), *S. cacaoi* var. *asoensis* (lysocellin), *S. cinnamonensis* (monensin), *S. aureofaciens* (narasin), *S. gallinarius* (RP 30504), *S. longwoodensis* (lysocellin), *S. flaveolus* (CP38936), *S. mutabilis* (S-11743a), and *S. violaceoniger* (nigericin).

Preferred host cells of restrictionless strains of Streptomyces taxa that produce glycopeptide antibiotics and in which the present vectors are especially useful and are transformed, include restrictionless cells of, for example: *S. orientalis* and *S. haranomachiensis* (vancomycin); *S. candidus* (A-35512, avoparcin), and *S. eburosporeus* (LL-AM 374).

Preferred host cells of other Streptomyces restrictionless strains in which the present vectors are especially useful and can be transformed, include restrictionless cells of, for example: *S. granuloruber, S. roseosporus, S. lividans, S. espinosus*, and *S. azureus*.

In addition to the representative Streptomyces host cells described above, the present vectors are also useful and can be transformed into E. coli. Thus, vectors of the present invention have wide application and are useful and can be transformed into host cells of a variety of organisms.

While all the embodiments of the present invention are useful, some of the present recombinant mants are preferred. DNA cloning vectors and transfor Accordingly, preferred vectors are pJL114, pJL121, pJL125, pJL180, pJL190, pJL192, pJL195, pJL197, pJL199 and pHJL212 and preferred transformants are *Streptomyces griseofuscus*/pJL114, *S. griseofuscus*/pJL121, *S. griseofuscus*/pJL125, *S. griseofuscus*/pJL180 *S. griseofuscus*/pJL190, *S. griseofuscus*/pJL192, *S. griseofuscus*/pJL195, *S. griseofuscus*/pJL199, *S. griseofuscus*/pJL197, *S. griseofuscus*/pHJL212, *E. coli* K12 C600$R_k$-$M_k$-/pJL114, *E. coli* K12 C600$R_k$-$M_k$-/pJL121, *E. coli* K12 C600$R_k$-$M_k$-/pJL125, *E. coli* K12 C600$R_k$-$M_k$-/pJL180, K12 C600$R_k$-$M_k$-/pJL190, *E. coli* K12 C600$R_k$-$M_k$-/pJL180, *E coli* K12 C600$R_k$-$M_k$-/pJL195, *E. coli* K12 C600$R_k$-$M_k$-/pJL199, *E. coli* K12 C600$R_k$-$M_k$-/pJL197, and *E. coli* K12 C600$R_k$-$M_k$-/pHJL212. Moreover, of this preferred group, plasmids pJL190, pJL192, pJL195, pJL197, pJL199 and pHJL212 and transformants *S. griseofuscus*/pJL190, *S. griseofuscus*/pJL192, *S. griseofuscus*/pJL195, *S. griseofuscus*/pJL197, *S. griseofuscus*/pJL199, *S. griseofuscus*/pHJL212, *E. coli* K12 C600$R_k$-$M_k$-/ pJL190, *E. coli* K12 C600$R_k$-$M_k$-/C600$R_k$-$M_k$-/pJL195 and *E. coli* K12 C600$R_k$-$M_k$-/pJL199 and *E. Coli* K12 C600Rk-Mk-/pJL199 and E. coli K12 C600Rk-Mk-/pHJL212 are most preferred. *Streptomyces griseofuscus* is a preferred host because it does not contain an endogenous plasmid or synthesize an antibiotic. Therefore, transformants of *S. griseofuscus* can be screened for clones that express genes for antibiotic synthesis.

The vectors of the present invention comprises origins of replication that are functional in *E. coli* and Streptomyces and therefore provide flexibility in the choice of hosts. Consequently, cloned DNA sequences can be shuttled into *E. coli* for construction of new plasmids, physical analysis, and for mapping of restriction sites and then shuttled back into Streptomyces for functional analysis and improvement of strains. This is particularly advantageous because amplification and manipulation of plasmids can be done faster and more conveniently in *E. coli* than in Streptomyces. For example, the present vectors can be amplified conventionally in *E. coli* K12 by growth with spectinomycin or chloramphenicol. This is not possible in the Streptomyces host system. In addition, since all the plasmid vectors contain resistance markers that are expressed in *E. coli* K12, recombinants are easily selected. Therefore, large amounts of plasmid DNA can be isolated conveniently and in a shorter time than that required for doing similar procedures in Streptomyces. Thus, after desired recombinant DNA procedures are accomplished in the E. coli host system, the particular Streptomyces DNA can be removed, reconstructed to plasmid form (if necessary), and then transformed into a Streptomyces host cell. Since the present vectors are fully selectable in Streptomyces, identification of recombinant clones can be done efficiently.

The recombinant DNA cloning vectors and transformants of the present invention have broad utility and help fill the need for suitable cloning vehicles for use in Streptomyces and *E. coli*. Moreover, the ability of the present vectors to confer a pock phenotype or resistance to antibiotics also provides a functional means for selecting transformants. This is important because of the practical necessity for determining and selecting the particular cells that have acquired vector DNA. Additional DNA segments, that lack functional tests for their presence, can also be inserted into the present vectors and then transformants containing the non-selectable DNA can be isolated by appropriate antibiotic or other phenotype selection. Such non-selectable DNA segments can be inserted at any site, except within regions necessary for plasmid function and replication, and include genes that specify antibiotic modification enzymes and regulatory genes of all types.

More particularly, a non-selectable DNA segment that comprises a gene can be inserted into a plasmid such as, for example, illustrative plasmid pJL192, at the internal BamHI restriction site of the ~7.7kb EcoRI-HindIII resistance-conferring fragment. Such an insertion inactivates the neomycin resistance gene and thus allows for the easy identification of Streptomyces transformants containing the recombinant plasmid. This is done by first selecting for M pock morphology and, secondarily, identifying those M transformants that are not resistant to neomycin. In a similar manner, insertion of a DNA segment into illustrative plasmid pJL180 at, for example, the unique PstI restriction site, inactivates the ampicillin resistance gene Thus, *E. coli* transformants carrying this recombinant plasmid can also be identified easily by first selecting for chloramphenicol resistance and, secondarily, identifying those chloramphenicol resistant transformants that are not resistant to ampicillin. Therefore, the ability to select for antibiotic resistance or other phenotypic markers in Streptomyces and *E. coli* allows for the efficient isolation of the extremely rare cells that contain the particular non-selectable DNA of interest.

The functional test for antibiotic resistance, as described above, can also be used to identify DNA segments that act as control elements and direct expression of an individual antibiotic resistance gene. Such segments, including but not limited to, promoters, attenuators, repressors, inducers, ribosomal binding sites, and the like, can be used to control the expression of other genes in cells of Streptomyces and *E. coli*.

The antibiotic resistance-conferring vectors of the present invention are also useful for insuring that linked DNA segments are stably maintained in host cells over many generations. These genes or DNA fragments, covalently linked to an antibiotic resistanceconferring fragment and propagated either in Streptomyces or *E. coli*, are maintained by exposing the transformants to levels of antibiotic that are toxic to non-transformed cells. Therefore, transformants that lose the vector, and consequently any covalently linked DNA, cannot grow and are eliminated from the culture. Thus, the vectors of the present invention can be used to maintain any DNA sequence of interest.

The cloning vectors and transformants of the present invention provide for the cloning of genes to improve yields of various products that are currently produced in Streptomyces and related cells. Examples of such products include, but are not limited to, Streptomycin, Tylosin, Cephalosporins, Actaplanin, Narasin, Monensin, Apramycin, Tobramycin, Erythromycin, and the like. The present invention also provides selectable vectors that are useful for cloning, characterizing, and reconstructing DNA sequences that code for commercially important proteins such as, for example, human insulin, human proinsulin, human growth bovine growth hormone, glucagon, interferon, and the like; for enzymatic functions in metabolic pathways leading to commercially important processes and compounds; or for control elements that improve gene expression. These desired DNA sequences include, but are not limited to, DNA that codes for enzymes that catalyze synthesis of derivatized antibiotics such as, for example, Streptomycin, Cephalosporin, Tylosin, Actaplanin, Narasin, Monensin, Apramycin, Tobramycin, and Erythromycin derivatives, or for enzymes that mediate and increase bioproduction of antibiotics or other products.

The capability of inserting, stabilizing, and shuttling the aforementioned DNA segments into Streptomyces and *E. coli* allows for easy recombinant genetic manipulation for increasing the yield and availability of antibiotics that are produced by Streptomyces. In addition, since the plasmid SCP2 or SCP2* origin of replication codes for low copy number, almost any DNA sequence, including those that are lethal when expressed from a high copy number plasmid, can be readily cloned into the present vectors and shuttled between Streptomyces and *E. coli*.

*Streptomyces coelicolor* A3(2) and *S. coelicolor* M110, as respective sources of plasmids SCP2 and SCP2*, can be cultured in a number of ways using any of several different media. Carbohydrate sources which are preferred in a culture medium include, for example, molasses, glucose, dextrin, and glycerol, and nitrogen sources include, for example, soy flour, amino acid mixtures, and peptones. Nutrient inorganic salts are also incorporated and include the customary salts capable of yielding sodium, potassium, ammonium, calcium, phosphate, chloride, sulfate, and like ions. As is necessary for the growth and development of other microorganisms, essential trace elements are also added. Such trace elements are commonly supplied as impurities incidental to the addition of other constituents of the medium.

*Streptomyces coelicolor* M110 and *S. coelicolor* A3 (2) are grown under aerobic culture conditions a relatively wide pH range of about 5 to 9 at temperatures ranging from about 15° to 40° C. For production of plasmids SCP2 and SCP2* at highest copy number, however, it is desirable to start with a culture medium at a pH of about 7.2 and maintain a culture temperature of about 30° C. Culturing *Streptomyces coelicolor* M110 and *S. coelicolor* A3(2) under the aforementioned conditions, results in a reservoir of cells from which plasmids SCP2 and SCP2* are respectively isolated conveniently by techniques well known in the art.

The following examples further illustrate and detail the invention disclosed herein. Both an explanation of and the actual procedures for constructing the invention are described where appropriate.

EXAMPLE 1

Isolation of Plasmid SCP2*

A. Culture of *Streptomyces coelicolor* M110

A vegetative inoculum of *Streptomyces coelicolor* M110 (NRRL 15041) was conventionally prepared by growing the strain under submerged aerobic conditions in 50 ml. of sterilized trypticase soy broth* at 35 g./l. in deionized water.

*Trypticase soy broth is obtained from Difco Laboratories, Detroit, Mich.

The trypticase soy broth inoculum was incubated for 48 hours at a temperature of 30° C. The 50 ml. culture was then homogenized, transferred to 450 ml. of sterilized YEMESG** medium, and then incubated for at least 40, but not more than 65 hours, at 30° C. The pH was not adjusted. After incubation, the *Streptomyces coelicolor* M110 cells were ready for harvest and subsequent isolation of plasmid DNA.

**YEMESG comprises, 0.3% yeast extract, 0.5% peptone, 0.3% malt extract, 1% dextrose, 34% sucrose, 0.1% $MgCl_2$, and 0.1% glycine.

B. Plasmid Isolation

About 10 g. (wet wgt) of *Streptomyces coelicolor* M110 cells were harvested by centrifugation (10 minutes, 4° C., 10,000 rpm) and then about 10 ml./g. wet wgt cells of TES buffer (0.01M Tris(hydroxymethyl)aminoethane [tris], 0.001M EDTA, 25% sucrose, pH 8) were added. The cells were vortexed into suspension followed by addition of 10 ml./g. wet wgt cells of .25M EDTA, pH 8 and then 5 ml./g. wet wgt cells of lysozyme (10 mg./ml. in TES). After the mixture was incubated at 37° C. for about 15 minutes, about 1.5 ml./g. wet wgt cells of 20% SDS (sodium lauryl sulfate (BDH Chemicals Ltd. Poole, Endland), were added. The resultant mixture was allowed added. The resultant mixture was allowed to stand at room temperature for 30 minutes, and then 5M NaCl was added to give a final concentration of 1M NaCl. After standing again at room temperature (15 minutes), the mixture was placed on ice for 2 hours. The lysate was centrifuged (20 minutes, 4° C., 17,500 rpm) and the supernatant was pooled and mixed with 0.64 volumes of isopropyl alcohol. The DNA precipitate was collected by centrifugation (15 minutes, 4° C., 10,000 rpm). The precipitate was air dried and then resuspended in 1 ml./g. wet wgt cells of TE buffer 0.01M Tris, 0.001M EDTA). Centrifugation (20 hours, 20° C., 50,000 rpm) using cesium chloride gradients with propidium iodide was carried out to purify the plasmid DNA. Following centrifugation, the desired plasmid SCP2* DNA band was removed and the propidium iodide extracted by conventional procedures. The CsCl-DNA solution was stored at −20° C. Prior to use, the DNA was desalted by either PD10 (Bio Rad) column exchange with TE or by dialysis against TE. The DNA was precipitated with ethanol by conventional procedures and redissolved in TE.

EXAMPLE 2

Construction of Plasmid pLR1

A. HindIII Digestion of Plasmid pIJ2

About 20 μl (20 μg.) of plasmid pIJ2 DNA, disclosed in Thompson et al., 1980, Nature 286:525, 5 μl BSA(Bovine Serum albumin, 1 mg./ml.), 19 μl water, 1 μl of HindIII (containing 3 New England Bio Labs units) restriction enzyme*, and 5 μl reaction mix** were incubated at 37° C. for 2 hours. The reaction was terminated by the addition of about 50 μl of 4 M ammonium acetate and 200 μl of 95% ethanol. The resultant DNA precipitate was washed twice in 70% ethanol, dried in vacuo, suspended in 20 μl of TE buffer, and frozen at −20° C. for storage.

*Restriction and other enzymes can be obtained from the following sources:
New England Bio Labs., Inc.
32 Tozer Road
Beverly, Massachusetts 01915
Boehringer-Mannheim Biochemicals
7941 Castleway Drive
Indianapolis, Indiana 46250
Bethesda Research Laboratories (BRL)

Box 6010
Rockville, Maryland 20850
Research Products
Miles Laboratories, Inc.
Elkhart, Indiana 46515
Reaction mix for HindIII restriction enzyme was prepared with the following composition:
600 mM NaCl
100 mM Tris-HCl, pH7.9
70 mM MgCl$_2$
10 mM Dithiothreitol

B. HindIII Digestion of Plasmid pBR322

About 8 μl (4 μg.) of plasmid pBR322 DNA, 5μl reaction mix, 5 μl BSA (1 mg./ml.), 31 μl water, and 1 μl of HindIII restriction enzyme were incubated at 37° C. for 2 hours. After the reaction was terminated by incubating at 60° C. for 10 minutes, about 50 μl of ammonium acetate and 200 μl of 95% ethanol were added. The resultant DNA precipitate was washed twice in 70% ethanol, dried in vacuo, and suspended in 45 μl of water.

C. Ligation of HindIII Digested Plasmids pIJ2 and pBR322

About 20 μl of HindIII treated plasmid pIJ2 (from Example 2A), 20 μl of HindIII treated plasmid pBR322 (from Example 2B), 5 μl BSA (1 mg./ml.), 1 μl of T4 DNA ligase*, and 5 μl ligation mix** were incubated at 16° C. for 4 hours. The reaction was terminated by the addition of about 50 μl 4M ammonium acetate and 200 μl of 95% ethanol. The resultant DNA precipitate was washed twice in 70% ethanol, dried in vacuo, and suspended in TE buffer. The suspended DNA constituted the desired plasmid pLR1.
T4 DNA ligase can be obtained from the following source:
New England Bio Labs., Inc.
32 Tozer Rd.
Beverly, Massachusetts 01915
Ligation mix was prepared with the following composition:
500mM Tris-HCl, pH7.8
200mM Dithiothreitol
100 mM MgCl$_2$
10mM ATP

EXAMPLE 3

Construction of *E. coli* K12 HB101/pLR1

About 10 ml. of frozen competent *E. coli* K12 HB101 cells (Bolivar et al., 1977, Gene 2:75-93) were pelleted by centrifugation and then suspended in about 10 ml of 0.01M sodium chloride. Next, the cells were pelleted again, resuspended in about 10 ml. of 0.03M calcium chloride, incubated on ice for 20 minutes, pelleted a third time, and finally, resuspended in 1.25 ml of 0.03M calcium chloride. The resultant cell suspension was competent for subsequent transformation.

Plasmid pLR1 in TE buffer (prepared in Example 2C) was ethanol precipitated, suspended in 150 μl of 30mM calcium chloride solution, and gently mixed in a test tube with about 200 μl of competent *E. coli* K12 HB101 cells. The resultant mixture was incubated on ice for about 45 minutes and then at 42° C. for about 1 minute. Next, about 3 ml. of L-broth (Bertani, 1951, J. Bacteriology 62:293) containing 50 μg./ml. of ampicillin was added. The mixture was incubated with shaking at 37° C. for 1 hour and then plated on L-agar (Miller, 1972, Experiments in Molecular Genetics, Cold Spring Harbor Labs, Cold Spring Harbor, N.Y.) containing ampicillin. Surviving colonies were selected and tested for the expected phenotype (Amp$^R$, Tet$^S$), and constituted the desired *E. coli* K12 HB101/pLR1 transformants.

EXAMPLE 4

Construction of Plasmid pLR4

A. Partial BamHI Digestion of Plasmid pLR1

About 10 μl (10 μg.) of plasmid pLR1, 5 μl BSA (1 mg./ml.), 29 μl water, 1 μl of BamHI (diluted 1:4 with water) restriction enzyme, and 5 μl reaction mix* were incubated at 37° C. for 15 minutes. The reaction was terminated by the addition of about 50 μl of 4M ammonium acetate and 200 μl of 95% ethanol. The resultant DNA precipitate was washed twice in 70% ethanol, dried in vacuo, and suspended in 20 μl water.
Reaction mix for BamHI restriction enzyme was prepared with the following composition:
1.5M NaCl
60mM Tris-HCl, p$^H$7.9
60mM MgCl$_2$

B. BamHI Digestion of Plasmid pBR322

The desired digestion was carried out in substantial accordance with the teaching of Example 2B except that BamHI restriction enzyme and reaction mix were used in place of HindIII restriction enzyme and reaction mix. The digested plasmid pBR322 was suspended in 29 μl of water.

C. Ligation of Partial BamHI Digested Plasmid pLR1 and BamHI Digested Plasmid pBR322

The desired ligation was carried out in substantial accordance with the teaching of Example 2C. The resultant ligated DNA was suspended in TE buffer and constituted the desired plasmid pLR4.

EXAMPLE 5

Construction of *E. coli* K12 HB101/pLR4

The desired construction was carried out in substantial accordance with the teaching of Example 3 except that plasmid pLR4, rather than plasmid pLR1, was used for transformation. Surviving colonies were selected and tested for the expected phenotype (Amp$^R$, Tet$^S$), and constituted the desired *E. coli* K12 HB101/ pLR4 transformants.

EXAMPLE 6

Construction of Plasmids pJL120 and pJL121

A. EcoRI Digestion of Plasmid SCP2*

About 150 μl (5.7 μg.) of plasmid SCP2* DNA, 1 μl. water, 2 μl of EcoRI (containing 20 BRL units) restriction enzyme, and 17 μl EcoRI reaction mix* were incubated at 37° C. for 2.5 hours. The reaction was terminated by incubation at 65° C. for 15 minutes. The reaction was conventionally analyzed by agarose gel electrophoresis (AGE) to verify that restriction was complete. The restricted DNA was stored at 4° C. for subsequent use.
*Reaction mix for EcoRI restriction enzyme was prepared with the following composition:
500mM NaCl
1000mM Tris-HCl, pH7.5
100mM MgCl$_2$

B. EcoRI Digestion of Plasmid pBR325

The desired digestion was carried out in substantial accordance with the teaching of Example 6A except that plasmid pBR325, rather than plasmid SCP2*, was used. The resultant DNA was stored at 4° C. for subsequent use.

C. Ligation of EcoRI Digested Plasmids SCP2* and pBR325

About 40 μl of EcoRI digested plasmid SCP2* (from Example 6A), 10 μl of EcoRI digested plasmid pBR325 (from Example 6B), 10 μl of MgCl₂ (0.1M), 10 μl. of (NH₄)₂SO₄ (0.1 M), 10 μl ATP (2mM) 0.1 μl of T4 DNA ligase, and 20 μl ligation mix* were incubated at 4° C. for 18 hours. The reaction was analyzed by AGE to verify appropriate ligation. The suspended DNA constituted the desired ~35.8kb plasmids pJL120 and pJL121.

Figure 2:
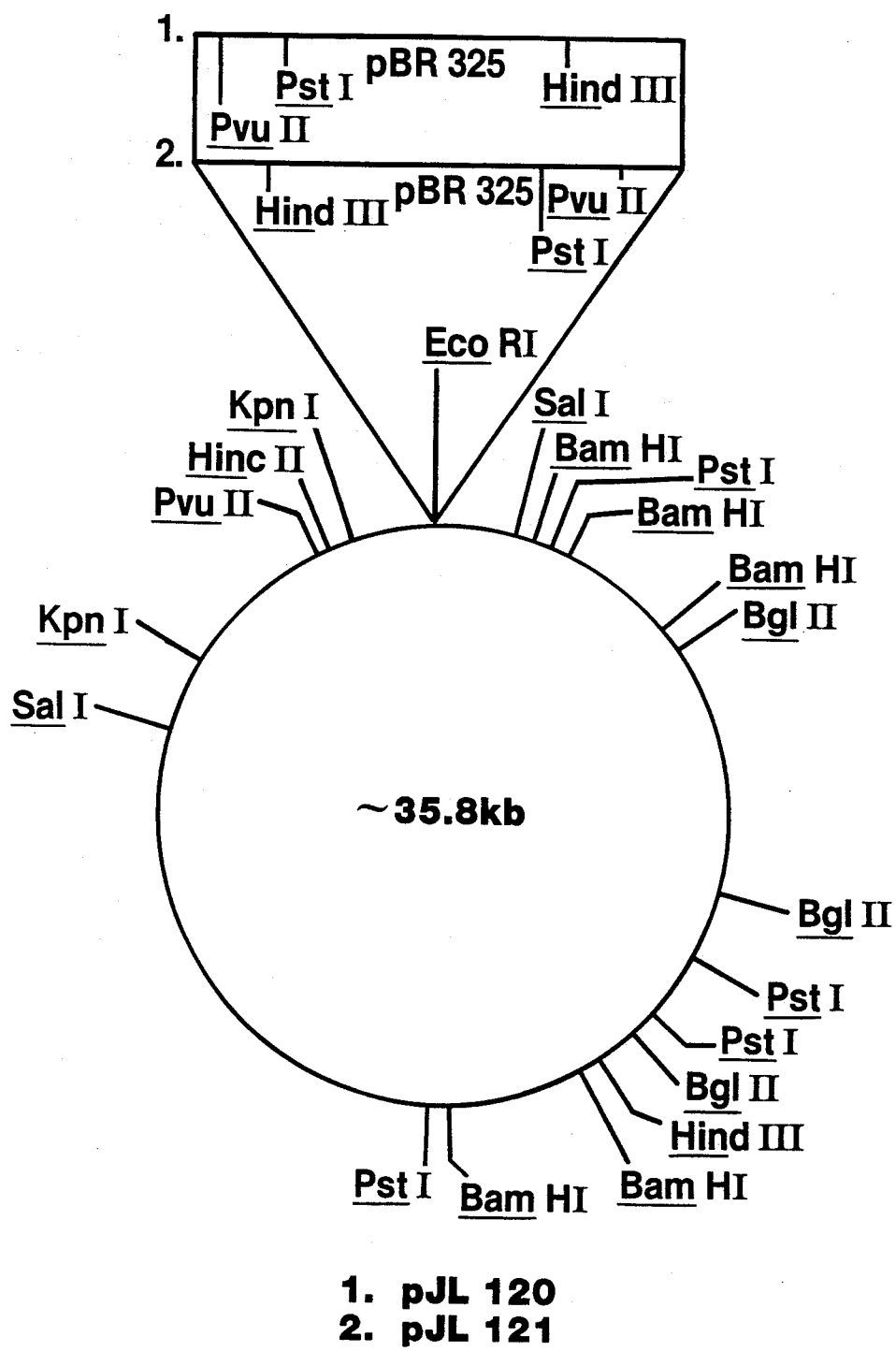
FIG. 2 shows restriction maps of pJL120 and pJL121.

Recombinant plasmids of two orientations result because the plasmid pBR325 EcoRI fragment can be oriented in either direction. A restriction site map of each of plasmids pJL120 and pJL121 was determined (after isolation as disclosed in Example 7) and is presented in FIG. 2 of the accompanying drawings.

*Ligation mix was prepared with the following composition:
50mM Tris-HCl, pH 7.5
10mM β-mercaptoethanol
1 mM EDTA
50 μg./ml. BSA

EXAMPLE 7

Construction of *E. coli* K12 C600R$_k$-M$_k$-/pJL120 and *E. coli* K12 C600R$_k$-M$_k$-/pJL121

A. Preparation of Frozen Competent *E coli* K12 C600R$_k$-M$_k$

Fresh overnight cultures of *E coli* K12 C600R$_k$-M$_k$- (disclosed in Chang and Cohen, 1974, Proc. Nat. Acad. Sci. 71:1030–1034) were subcultured 1:10 in fresh L-broth (disclosed in Miller, 1972, Experiments in Molecular Genetics, Cold Spring Harbor Labs, Cold Spring Harbor, New York) and grown at 37° C. for 1 hour. A total of 660 Klett Units of cells were harvested, washed with 2.5 ml. of 100mM NaCl₂, suspended in 150mM CaCl₂ with 10% glycerol, and incubated at room temperature for 20 minutes. The cells were harvested by centrifugation, resuspended in 0.5 ml. of CaCl₂-glycerol, chilled on ice for 3–5 minutes and frozen. The suspensions of cells were stored in liquid nitrogen until use. Preservation and storage did not adversely affect the viability or frequency of transformation by covalently closed circular DNA.

B. Transformation

The competent cells were thawed in an ice bath and mixed in a ratio of 0.1 ml. of cells to 0.05 ml of DNA (10 μl of the sample disclosed in Example 6C and 40 μl of 0.1XSSC (0.015M NaCl 0.0015M Sodium Citrate at pH 7). The transformation mixture was chilled on ice for 20 minutes, heat shocked at 42° C. for 1 minute and chilled on ice for 10 minutes. The samples were diluted with 0.85 ml. of L-broth, incubated at 37° C. for 1.5 hours, spread on L-agar containing ampicillin (50 μg./ml.) and tetracycline (12.5 μg/ml.) and incubated for 18 hours at 37° C. The resultant colonies were selected and tested for the expected phenotype (Amp$^R$, Tet$^R$, CM$^S$) and constituted the desired *E. coli* K12 C600R$_k$-M$_k$-/pJL120 and *E. coli* K12 C600R$_k$-M$_k$-/pJL121 transformants. The ampicillin and tetracycline resistant colonies were isolated according to known procedures, cultured, and then conventionally identified by restriction enzyme and AGE analysis of the constitutive plasmids. The identified transformants were then used for subsequent production and isolation of plasmids pJL120 and pJL121 according to known procedures.

EXAMPLE 8

Construction of Plasmids pJL180 and pJL181

A. SalI Digestion of Plasmid SCP2* and Isolation of ~6.0kb SalI Fragment

The desired digestion was carried out in substantial accordance with the teaching of Example 6 except SalI restriction enzyme and reaction mix*, rather than EcoRI restriction enzyme and reaction mix, were used. The reaction was assayed by AGE to verify completion and terminated by heating at 65° C. for 15 minutes. The resultant SalI restriction fragments were separated by AGE and then the separated fragments were located in the gel by staining with ethidium bromide and visualizing fluorescent bands with an ultraviolet light. The gel fragment containing the ~m 6.0kb fragment of interest was excised from the gel and electroeluted into TBE buffer (1.6% Sigma 7-9 buffer, 0.993% Na₂DETA, 0.55% boric acid). The gel-fragment in TBE buffer was in a dialysis bag and subjected to electrophoresis at 100v for 1 hour. The aqueous solution was collected from the dialysis bag and passed over a DEAE cellulose column* (0.5 ml. Whatman DE52) that had been equilibrated with equilibration buffer (0.1 M KCl, 10 mM Tris-HCl, pH 7.8). The column was washed with 2.5 ml. of equilibration buffer and the DNA (about 5 μg.) was eluted with 1.5 ml. of elution buffer (1M NaCl, 10 mM TrisHCl, pH 7.8). The eluent was adjusted to about .35M with respect to Na⁺ ion concentration, and then the DNA was precipitated by adding 2 volumes (about 9 ml.) of 100% ethanol followed by cooling to $-20°$ C. for 16 hours. The DNA precipitate was pelleted by centrifugation, washed with 75% ethanol, dried, and dissolved in TE buffer. Hereinafter, this conventional isolation technique is referred to as AGE/DE52/electroelution.

*Reaction mix for SalI restriction enzyme was prepared with the following composition:
1500 mM NaCl
80 mM Tris-HCl, pH7.5
60 mM MgCl2
2 mM EDTA
**Sigma 7-9 buffer can be obtained from Sigma Chemical Company, P.O. Box 14508, St. Louis, Mo. 63178
***DEAE cellulose (DE52) can be obtained from Whatman Inc., 9 Bridewell Place, Clifton, N.J. 07014.

B. SalI Digestion of Plasmid pBR325

The desired digestion was carried out in substantial accordance with the teaching of Example 8A except that plasmid pBR325 was employed and fragments were not separated by preparative AGE/DE52/electroelution. The resultant DNA was dissolved in TE buffer and stored at 4° C. for future use.

C. Ligation of SalI Digested Plasmid pBR325 and ~6.0kb SalI Fragment of Plasmid SCP2*

About 1.5 μg. of the 6.0kb SalI fragment of SCP2*, prepared in Example 8A, was mixed with 0.5 μg. of SalI digested pBR325, prepared in Example 8B. The DNA mixture was precipitated by standard ethanol precipitation and redissolved in 3 μl of distilled water, 4 μl of .66M ATP, 2 μl of ligase-kinase mixture (0.25M Tris.HCl, pH 7.8, 50 mM MgCl₂, 25 mM dithiothreitol and 25% glycerol) and 1 μl of T4-DNA ligase (1 unit). After incubation for 1 hour at 15° C., the reaction mixture was diluted with 12 μl of water, 20 μl of .66M ATP, 8 μl of ligase-kinase mixture and then incubated at 15° C. for 18 hours. The resultant ligated DNA was diluted 1:5 into .1XSSC and constituted the desired ~12.0kb plasmids pJL180 and pJL181.

Figure 3:
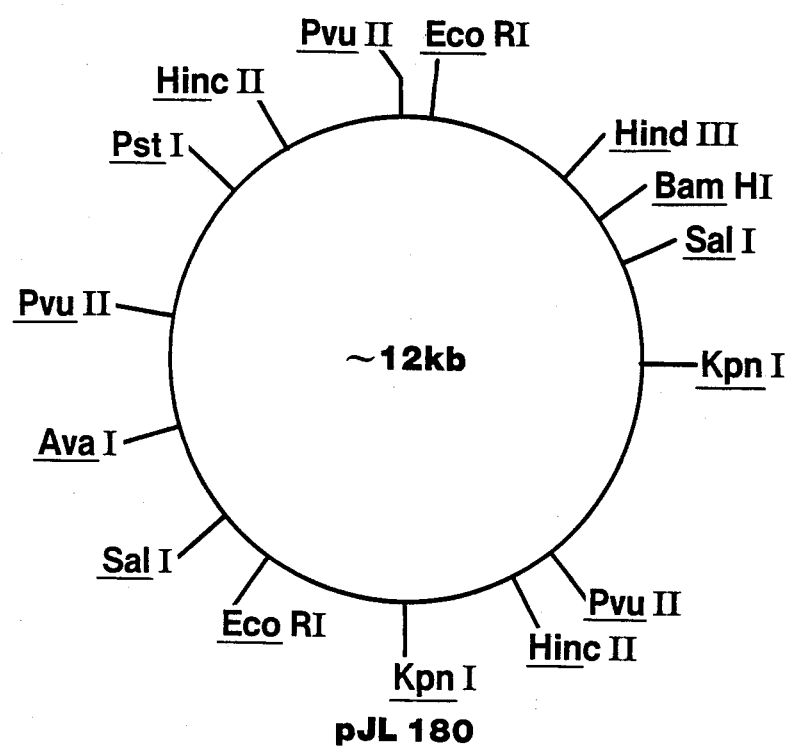
FIG. 3 shows restriction maps of pJL180 and pJL181.
Figure 3:
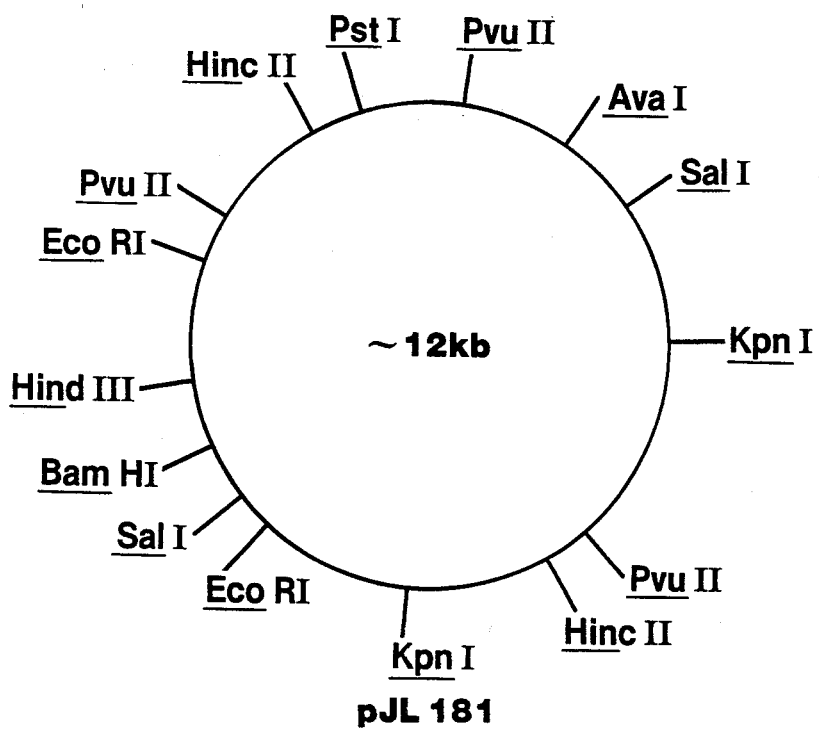

Recombinant plasmids of two orientations result because the plasmid pBR325 SalI fragment can be oriented in either direction. A restriction site map of each of plasmids pJL180 and pJL181 is presented in FIG. 3 of the accompanying drawings.

EXAMPLE 9

Construction of *E. coli* K12 C600R$_k$-M$_k$-/pJL180 and *E. coli* K12 C600R$_k$-M$_k$-/pJL181

The desired constructions were made in substantial accordance with the teaching of Example 7 except that the mixture of plasmid pJL180 and pJL181 DNA (from Example 8C), rather than plasmid pJL120 and pJL121, were used. The resultant transformant colonies were selected and tested for the expected phenotype (Amp$^R$, Tet$^S$, CM$^R$), and constituted the desired *E. coli* K12 C600R$_k$-M$_k$-/pJL180 and *E. coli* K12 C600R$_k$-M$_k$-/pJL181 transformants. The ampicillin and chloramphenicol resistant colonies were isolated according to known procedures, cultured, and then conventionally identified by restriction enzyme and AGE analysis of the constitutive plasmids. The identified transformants can then be used for subsequent production and isolation of plasmids pJL180 and pJL181 according to known procedures.

EXAMPLE 10

Construction of Plasmid pJL125

A. SalI Digestion of Plasmid pJL121 and Isolation of ~10.2kb SalI Fragment

The desired digestion was carried out in substantial accordance with the teaching of Example 8 except that the reaction was stopped before digestion was complete and except that plasmid pJL121, rather than plasmid SCP2*, was used. The resultant SalI fragments were not separated by preparative AGE but precipitated by standard ethanol precipitation. The restriction fragments were dissolved in TE buffer and immediately ligated.

B. Ligation of ~10.2kb SalI Fragment of Plasmid pJL121

Figure 4:
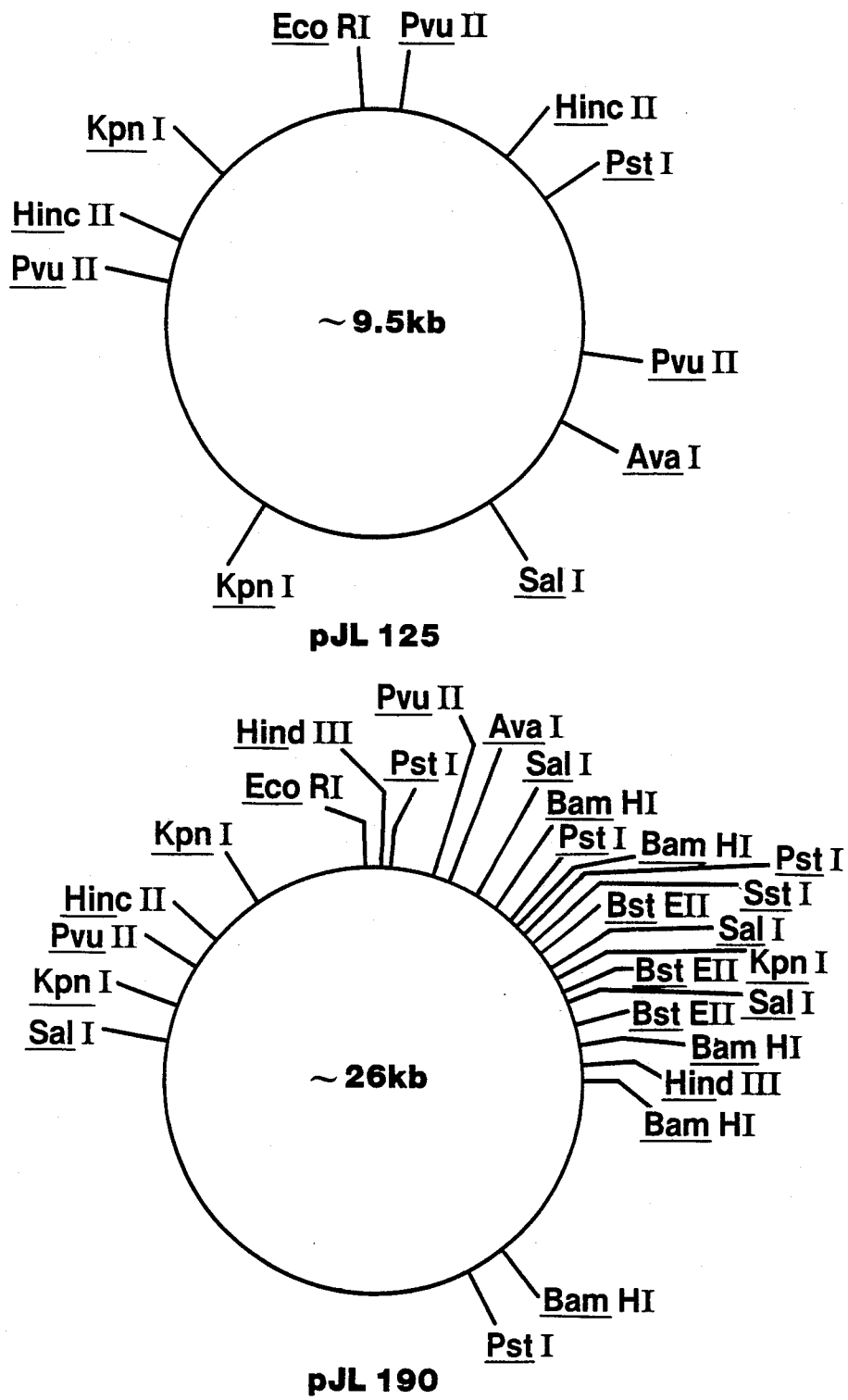
FIG. 4 shows restriction maps of pJL125 and pJL190.

The desired ligation was carried out in substantial accordance with the teaching of Example 8C except that the SalI fragments of plasmid pJL121, rather than the SalI fragment of plasmid SCP2* and pBR325, were used. The resultant ligated DNA constituted the desired plasmid pJL125 plus 12 other plasmids that were subsequently isolated and shown to contain additional SalI restriction fragments of pJL121. Plasmid pJL125, which was conventionally isolated and contains an origin of replication from plasmid pBR325 and also the ~5.4kb origin of replication-containing EcoRI-SalI fragment of plasmid SCP2*, was dissolved in TE buffer and stored at 4° C. for future use. A restriction site map of plasmid pJL125 is presented in FIG. 4 of the accompanying drawing. The restriction site map was determined with plasmid from transformed *E. coli* K12 C600R$_k$-M$_k$-.

EXAMPLE 11

Construction of *E. coli* K12 C600R$_k$-M$_k$-/pJL125

The desired construction was made in substantial accordance with the teaching of Example 7 except that plasmid pJL125, rather than plasmids pJL120 and pJL121, was used. The resultant colonies were selected and tested for the expected phenotype (Amp$^R$, Tet$^S$, CM$^S$) and constituted the desired *E. coli* K12 C600R$_k$-M$_k$-/pJL125 transformants. The identity of the transformants was further confirmed by AGE and restriction analysis by the procedure of Eckardt, 1978, Plasmid 1:584 and by Klein et al., 1980, Plasmid 3:88. The transformants were then conventionally cultured for subsequent production and isolation of plasmid pJL125 according to known procedures.

EXAMPLE 12

Construction of Plasmid pJL190

A. EcoRI-HindIII Digestion of Plasmid pJL121 and Isolation of ~19.0kb EcoRI-HindIII Fragment About 200 μl (80 μg.) of plasmid pJL121 DNA, 30 μl BSA (1 mg./ml.), 40 μl of HindIII (containing 200 BRL units) restriction enzyme, and 30 μl HindIII reaction mix* were incubated at 37° C. for about 3 hours and then at 65° C. for 10 minutes. The 300 μl reaction mixture was cooled to 4° C., supplemented with 110 μl of 10X HindIII→EcoRI diluent reaction mix** and 30 μl EcoRI restriction enzyme (containing 300 BRL units), and then incubated at 37° C. for 3 hours, then at 65° C. for 10 minutes followed by cooling to 4° C. The resultant ~19.0kb EcoRI-HindIII restriction fragment was conventionally isolated by AGE/DE52/electroelution. The desired DNA was dissolved in TE buffer and stored at 4° C. for future use.

*HindIII reaction mix was prepared with the following composition:
60mM Tris-HCl, pH 7.5
500mM NaCl
60mM MgCl$_2$
**HindIII→EcoRI diluent was prepared with the following composition:
382mM Tris-HCl, pH 7.5
50mM NaCl
22mM MgCl$_2$ B. EcoRI-HindIII Digestion of Plasmid pLR4 and Isolation of ~7.7kb EcoRI-HindIII Fragment The desired digestion and isolation was carried out in substantial accordance with the teaching of Example 12A except that plasmid pLR4, rather than plasmid pJL121, was used. The desired ~7.7kb fragment was dissolved in TE buffer and stored at 4° C. for future use.

C. Ligation of ~19.0kb EcoRI-HindIII Fragment of Plasmid pJL121 and ~7.7kb EcoRI-HindIII Fragment of Plasmid pLR4

The desired ligation was carried out in substantial accordance with the teaching of Example 8C except that the ~19.0kb EcoRI-HindIII fragment of plasmid pJL121 and the ~7.7 EcoRI-HindIII fragment of plasmid pLR4, rather than the 6.0kb SalI fragment of plasmid SCP2* and SalI digested pBR325, were used. The resultant ligated DNA constituted the desired plasmid pJl190 which was then stored at 4° C. for future use. A restriction site and functional map of plasmid pJL190 is presented in FIG. 4 of the accompanying drawings. The restriction site map was determined from plasmid transformed into *E. coli* K12 C600R$_k$-M$_k$-.

EXAMPLE 13

Construction of *E. coli* K12 C600R -M -/pJL190

The desired construction was made in substantial accordance with the teaching of Example 7 except that plasmid pJL190, rather than plasmids pJL120 and pJL121, was used. The resultant colonies were selected and tested for the expected phenotype (Amp$^R$, Tet$^S$) and size by conventional means (as in Example 11) and constituted the desired *E. coli* K12 C600R$_k$-M$_k$-/pJL190 transformants. The transformants were then conventionally cultured for subsequent production and isolation of plasmid pJL190 according to known procedures.

EXAMPLE 14

Isolation of Plasmid pJL192

Plasmid pJL192, which confers high resistance to antibiotic neomycin (10 μg./ml.), can be conventionally isolated from *E. coli* K12 C600R$_k$-M$_k$-/pJL192, a strain deposited and made part of the permanent stock culture collection of the Northern Regional Research Laboratory, Peoria, Ill. under the accession number 15040. The restriction site map of plasmid pJL192 appears not to be distinguishable from the plasmid pJL190 map presented in FIG. 4.

EXAMPLE 15

Construction of Plasmid pJL195

A. EcoRI-SalI Digestion of Plasmid pJL125 and Isolation of ~5.4kb EcoRI-SalI Fragment The desired digestion and isolation was carried out in substantial accordance with the teaching of Example 12A except that plasmid pJL125 and SalI restriction enzyme and reaction mix, rather than plasmid pJL121 and HindIII restriction enzyme and reaction mix, were used. In addition, SalI-EcoRI diluent* was used. The resultant ~5.4kb EcoRI-SalI fragment was dissolved in TE buffer and stored at 4° C. for future use.

*SalI-EcoRI diluent was prepared with the following composition:
940mM Tris-HCl, pH 7.5
55mM MgCl$_2$

B. EcoRI-Partial SalI Digestion of Plasmid pLR4 and Isolation of ~7.5kb EcoRI-Partial SalI Fragment The SalI digestion was carried out in substantial accordance with the teaching of Example 12A except plasmid pLR4, rather than pJL121, was used. Since only a partial SalI digestion was desired, the resultant mixture was incubated first at 37° C. for 15 minutes and then at 65° C. for 10 minutes. Following cooling to 4° C., the resultant partial SalI ~7.7kb linear fragment was conventionally isolated by AGE/DE52/electroelution. DE52/electroelation. The desired DNA was dissolved in TE buffer and digested with EcoRI restriction enzyme in substantial accordance with the teaching of Example 6A except that the above fragment, rather than plasmid SCP2*, was used. The desired ~7.5kb EcoRI-SalI fragment (the largest possible EcoRI-SalI fragment) was isolated by AGE/DE52/electroelution, dissolved in TE buffer, and then stored at 4° C. for future use.

C. Ligation of ~5.4kb EcoRI-SalI Fragment of Plasmid pJL125 and ~7.5kb EcoRI-Partial SalI Fragment of Plasmid pLR4

Figure 5:
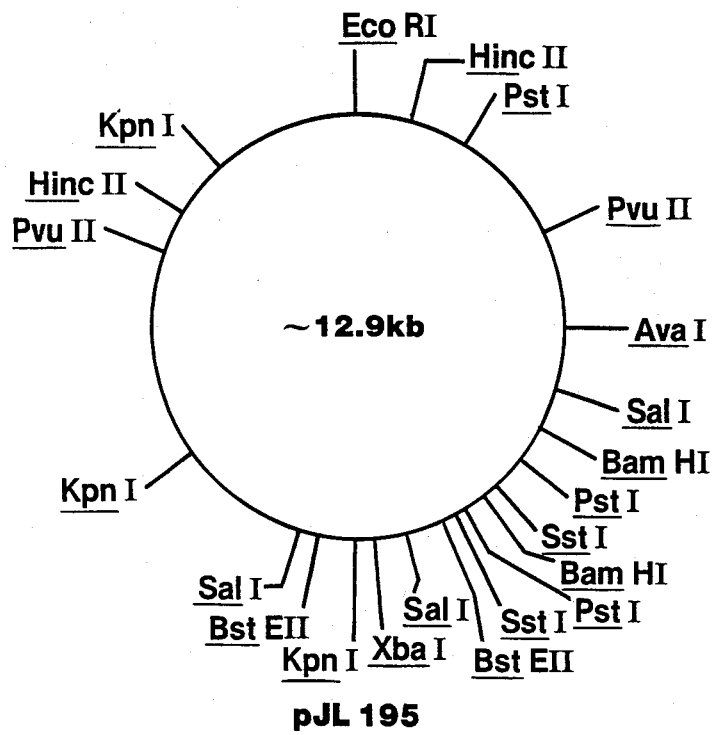
FIG. 5 shows restriction maps of pJL195 and pJL114.
Figure 5:
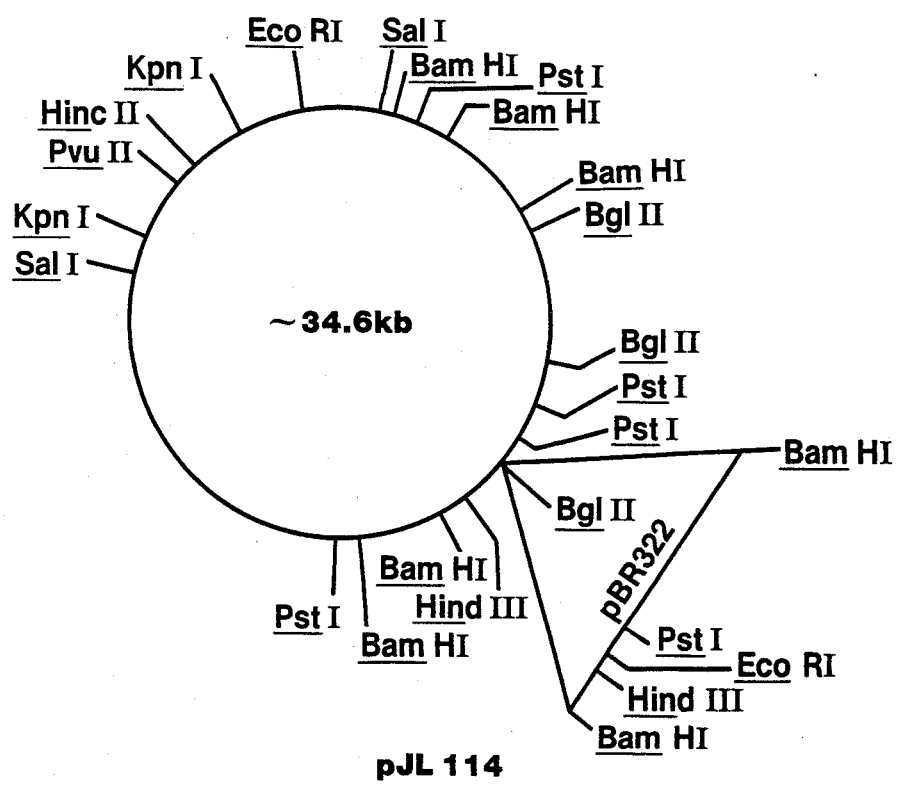

The desired ligation was carried out in substantial accordance with the teaching of Example 8C except that the ~5.4kb EcoRI-SalI fragment of plasmid pJL125 and the ~7.5kb EcoRI-partial SalI fragment of plasmid pLR4, rather than the ~6.0kb SalI fragment of plasmid SCP2* and SalI digested pBR325, were used. The resultant ligated DNA constituted the desired plasmid pJL195 and was stored at 4° C. for future use. A restriction site map of plasmid pJL195 is presented in FIG. 5 of the accompanying drawings. The restriction site map was determined with plasmid isolation from *E. coli* K12 C600R$_k$-M$_k$-.

EXAMPLE 16

Construction of *E coli* K12 C600R$_k$-M$_k$-/pJL195

The desired construction was made in substantial accordance with the teaching of Example 7 except that plasmid pJL195, rather than plasmids pJL120 and pJL121, was used. The resultant colonies were tested for the expected phenotype (Amp$^R$, Tet$^S$) and size (as in Example 11) and constituted the desired *E. coli* C600R$_k$-M$_k$-/pJL195 transformants. The transformants were then conventionally cultured for subsequent production and isolation of plasmid pJL195 according to known procedures.

EXAMPLE 17

Construction of Plasmid pJL114

A. Partial BamHI Digestion of Plasmid SCP2

The desired digestion was carried out in substantial accordance with the teaching of Example 6A except that plasmid SCP2 (isolated, in accordance with the teaching of Example 1, from *Streptomyces coelicolor* A3(2), a strain deposited and made part of the permanent stock culture collection of the Northern Regional Research Laboratory under the accession number 15042), and BamHI restriction enzyme and reaction mix*, rather than plasmid SCP2* and EcoRI restriction enzyme and reaction mix, were used. The desired DNA was stored at 4° C. for subsequent use.

*Reaction mix for BamHI restriction enzyme was prepared with the following composition:
1000mM Tris-HCl, pH 7.4
100mM MgClhd 2

B. Ligation of BamHI Digested Plasmid SCP2 and BamHI Digested Plasmid pBR322

The desired ligation was carried out in substantial accordance with the teaching of Example 6C except that the BamHI digest of plasmid SCP2 (prepared in Example 17A) and BamHI-digested plasmid pBR322 (prepared in Example 4B), rather than plasmids SCP2* and pBR325, were used. The resultant DNA was stored at 4° C. and constituted the desired ~34.6kb plasmid pJL114.

EXAMPLE 18

Construction of =*E. coli* K12 C600R$_k$-M$_k$-/pJL114

The desired construction was made in substantial accordance with the teaching of Example 7 except that plasmid pJL114, rather than plasmids pJL120 and pJL121, was used. The resultant colonies were selected and tested for the expected phenotype (Amp$^R$, Tet$^S$), and constituted the desired *E. coli* K12 C600R$_k$-M$_k$-/pJL114 transformants. The ampicillin resistant, tetracycline sensitive colonies were isolated according to known procedures, cultured, and then conventionally identified by restriction enzyme and agarose gel electrophoretic analysis of the constitutive plasmids.

It was revealed upon analysis that the BamHI restriction enzyme had cut only one of the BglII restriction sites of SCP2 during the digestion described in Example 17A. Since this event is rare and has not been repeated, *E. coli* K12 C600R$_k$-M$_k$-/pJL114 has been deposited and made part of the permanent stock culture collection of the Northern Regional Research Laboratory, Peoria, Ill. under the accession number B-15039. The strain is available as a preferred source and stock reservoir of plasmid pJL114. A restriction site map of plasmid pJL114 is presented in FIG. 5 of the accompanying drawings.

EXAMPLE 19

Construction of *Streptomyces griseofuscus*/pJL120

A. Growth of Cultures for Preparation of Protoplasts

A vegative innoculum was conventionally prepared by growing the strain under submerged conditions for 20 hours at 30° C. in TSB supplemented with 0.4% glycine. The culture was homogenized and innoculated at a 1/20 dilution into the same medium and then grown for 18 hours at 30° C.

B. Transformation

Using about 20 μg. of plasmid pJL120 DNA and $1 \times 10^9$ protoplasts of *Streptomyces griseofuscus*, a strain deposited and made part of the permanent stock culture collection of the American Type Culture Collection, Rockville, Md., from which it is available to the public under the accession number ATCC 23916, the desired transformation was carried out in substantial accordance with the teaching of International Publication (of International patent application No. PCT/BG79/00095) No. W079/01169, Example 2.

C. Selection

To assay for transformation even at low frequencies, two procedures were employed.

(1) Pock-assay:

Spores were harvested from the regeneration plates containing confluent lawns of regenerated protoplasts as follows. About 10 ml. of sterile distilled water were added to the plate and the surface of the culture gently scraped with a loop to remove the spores. The resulting spore suspension was centrifuged at 20,000 rpm for 10 minutes. The supernatant was discarded and the remaining spore pellet resuspended in 0.3 ml. of 20% v/v glycerol. Serial dilutions of the preparation were made down to $10^{-5}$ by successive transfer of 0.1 ml. of the spore suspension to 0.9 ml. of 20% v/v glycerol. The spores can then be stored at −20° C. with little loss of viability. About 0.1 ml. aliquots of some of the dilution series (e.g. $10^{-1}$, $10^{-2}$, $10^{-4}$) of each of the harvested plates were then transferred to R2 medium (Hopwood and Wright, 1978, Molecular and General Genetics 162:30) plates which had sufficient spores of the *Streptomyces griseofuscus* strain originally used in the transformation procedure to produce a confluent lawn. This procedure can also be carried out with the substitution of YMX agar (0.5% yeast extract 0.5% malt extract, 0.1% dextrose and 2% agar). Transformants can typically be detected after 3 days' growth at 30° C. by the appearance of "pocks", a property expressed by spores containing the plasmid in expressible form within the lawn. The transformants were recovered by conventionally picking spores from the centre of the "pock" to an agar plate of YMX medium (Hopwood 1967, Bacteriological Review, 31:373).

(2) Back transformation to *E. coli* K12 C600$R_k$-$M_k$-:

The spores are collected as in (1) above but are used to innoculate 50 ml. of TSB supplemented with 0.4% glycine. The culture is grown for 20 hours at 30° C. and the cells are harvested followed by isolation of DNA. Isolation is as disclosed in Example 1B except that centrifugation with CsCl and propidium iodide is omitted. Subsequently, 50 μl. of this DNA is used to transform *E. coli* K12 C600$R_k$-$M_k$- as disclosed in Example 7B. Plasmids in the transformants are verified and identified by conventional means as taught in Example 11.

EXAMPLE 20

Construction of *Streptomyces griseofuscus*/pJL114, *S. griseofuscus*/pJL121, *S. griseofuscus*/pJL125, *S. griseofuscus*/pJL180, and *S. griseofuscus*/pJL181.

The desired constructions were each individually and respectively made, selected, and recovered in substantial accordance with the teaching of Example 19 except that plasmids pJL114, pJL121, pJL125, pJL180, and pJL181, rather than plasmid pJL120, were appropriately used for the individual construction.

EXAMPLE 21

Construction of *Streptomyces griseofuscus*/pJL190

A. Transformation

The desired transformation was carried out in substantial accordance with the teaching of Example 19B except that plasmid pJL190, rather than plasmid pJL120, was used.

B. Selection

The desired transformants were selected for neomycin resistance by overlaying the regenerating protoplasts with R2 medium top agar containing sufficient neomycin to bring the final plate concentration to 1 μg./ml. The resultant *Streptomyces griseofuscus*/pJL190 transformants were then tested for the expected pock morphology in substantial accordance with the procedure of Example 19C.

EXAMPLE 22

Construction of *Streptomyces griseofuscus*/pJL195

The desired construction was made, selected, and recovered in substantial accordance with the teaching of Example 21 except that plasmid pJL195, rather than plasmid pJL190, was used.

EXAMPLE 23

Construction of *Streptomyces griseofuscus*/pJL192

The desired construction was made, selected, and recovered in substantial accordance with the teaching of Example 22 except that plasmid pJL192 and, in the selection procedure, top agar containing sufficient neomycin to bring the final plate concentration to 10 μg./ml., rather than plasmid pJL195 and top agar containing sufficient neomycin to bring the final plate concentration to 1 μg./ml., were used.

EXAMPLE 24

Construction of *Streptomyces fradiae*/pJL120, *S. fradiae*/pJL114, *S. fradiae*/pJL121, *S. fradiae*/pJL125, *S. fradiae*/pJL180, *S. fradiae*/pJL181, *S. fradiae*/pJL190, *S. fradiae*/pJL195, and *S. fradiae*/pJL192

The desired constructions are individually and respectively made, selected, and recovered in substantial accordance with the respective teachings of Examples 19, 20, 21, 22, and 23 except that *Streptomyces fradiae*, rather than *S. griseofuscus*, is used. In addition, the TSB medium for protoplasting and growing *S. fradiae* was modified and contained only 0.2% glycine.

EXAMPLE 25

Construction of *Streptomyces lividans*/pJL120, *S. lividans*/pJL114, *S. lividans*/pJL121, *S. lividans*/pJL125, *S. lividans*/pJL180, *S. lividans*/pJL181, *S. lividans*/pJL190, *S. lividans*/pJL195, and *S. lividans*/pJL192

The desired constructions are individually and respectively made, selected, and recovered in substantial accordance with the respective teachings of Examples 19, 20, 21, 22, and 23 except that *Streptomyces lividans*, rather than *S. griseofuscus*, is used. In addition, the media for protoplasting and growing *S. lividans* is as described in International Publication (of International patent application No. PCT/BG79/00095) No. WO79/01169, Example 2.

EXAMPLE 26

Isolation of Plasmid pJL192 Mutant that Confers High Resistance To Antibiotic Neomycin

*Streptomyces griseofuscus*/pJL190 was isolated as described in Example 21. Analysis of growth of colonies on nutrient agar supplemented with different concentrations of neomycin revealed that *S. griseofuscus*/pJL190 exhibited resistance to 1.0 µg./ml. of neomycin. *S. griseofuscus* was spread conventionally on nutrient agar plates supplemented with 10 µg./ml. of neomycin. A colony was discovered that exhibited growth at this high level of neomycin. After repeated analysis verified that the colony exhibited the aforementioned resistance, the colony was designated *S. griseofuscus*/pJL192. The plasmid, pJL192 was shuttled into *E. coli* K12 C600R$_k$-M$_k$- by back transformation as taught in Example 19C. The restriction site map of pJL192 appears not to be distinguishable from pJL190.

EXAMPLE 27

Isolation of Plasmid pJL199 Mutant that Confers High Resistance to Antibiotic Neomycin The desired isolation is carried out in substantial accordance with the teaching of Example 26 except that *Streptomyces griseofuscus*/pJL195 (prepared in Example 22), rather than *S. griseofuscus*/pJL190, was used. A colony that exhibited high resistance to neomycin was designated *S. griseofuscus*/pJL199. The plasmid, pJL199, was shuttled into *E. coli* K12 C600R$_k$-M$_k$- by back transformation as taught in Example 19C. The restriction site map of pJL199 appears not to be distinguishable from pJL195.

Those skilled in the art will recognize that plasmid pJL199 can also be conventionally constructed by substituting the neomycin resistance-conferring fragment of plasmid pJL192 (prepared in Examples 15 and 27) for the pLR4-derived neomycin resistance-conferring fragment of plasmid pJL195. Such a substitution thus also results in the desired plasmid pJL199.

EXAMPLE 28

Construction of Plasmid pLR2

A. HindIII Digestion of Plasmid pIJ6

About 20 µl. (20µg.) of plasmid pIJ6 DNA, disclosed in Thompson et al., 1980, Nature 286:525, 5 µl. BSA(Bovine Serum albumin, 1 mg./ml.), 19 µl. water, 1 µl. of HindIII (containing 3 New England Bio Labs units) restriction enzyme*, and 5 µl. reaction mix** were incubated at 37° C. for 2 hours. The reaction was terminated by the addition of about 50 µl. of 4M ammonium acetate and 200 µl. of 95% ethanol. The resultant DNA precipitate was washed twice in 70% ethanol, dried in vacuo, suspended in 20 µl. of TE buffer, and frozen at −20° C. for storage.

B. HindIII Digestion of Plasmid pBR322

About 8 µl. (4 µg.) of plasmid pBR322 DNA, 5 µ. reaction mix, 5 µ. BSA (1 mg./ml.), 31 µ. water, and 1 µ. of HindIII restriction enzyme were incubated at 37° C. for 2 hours. After the reaction was terminated by incubating at 60° C. for 10 minutes, about 50 µ. of ammonium acetate and 200 µ. of 95% ethanol were added. The resultant DNA precipitate was washed twice in 70% ethanol, dried in vacuo, and suspended in 45 µ. of water.

C. Ligation of HindIII Digested Plasmids pIJ6 and pBR322

About 20 µ. of HindIII treated plasmid pIJ6 (from Example 28A), 20 µ. of HindIII treated plasmid pBR322 (from Example 28B), 5 µ. BSA (1 mg./ml.), 1 µ. of T4 DNA ligase*, and 5 µ. ligation mix** were incubated at 16° C. for 4 hours. The reaction was terminated by the addition of about 50 µ. 4M ammonium acetate and 200 µ. of 95% ethanol. The resultant DNA precipitate was washed twice in 70% ethanol, dried in vacuo, and suspended in TE buffer. The suspended DNA constituted the desired plasmid pLR2.

EXAMPLE 29

Construction of *E. coli* K12 HB101/pLR2

About 10 ml. of frozen competent *E. coli* K12 HB101 cells (Bolivar et al., 1977, Gene 2:75-93) were pelleted by centrifugation and then suspended in about 10 ml. of 0.01M sodium chloride. Next, the cells were pelleted again, resuspended in about 10 ml. of 0.03M calcium chloride, incubated on ice for 20 minutes, pelleted a third time, and finally, resuspended in 1.25 ml. of 0.03M calcium chloride. The resultant cell suspension was competent for subsequent transformation.

Plasmid pLR2 in TE buffer (prepared in Example 28C) was ethanol precipitated, suspended in 150 µ. of 30 mM calcium chloride solution, and gently mixed in a test tube with about 200 µ. of competent *E. coli* K12 HB101 cells. The resultant mixture was incubated on ice for about 45 minutes and then at 42° C. for about 1 minute. Next, about 3 ml. of L-broth (Bertani, 1951, J. Bacteriology 62:293) containing 50 µg./ml. of ampicillin were added. The mixture was incubated with shaking at 37° C. for 1 hour and then plated on L-agar (Miller, 1972, Experiments in Molecular Genetics, Cold Spring Harbor Labs, Cold Spring Harbor, N.Y.) containing ampicillin. Surviving colonies were selected and tested for the expected phenotype (Amp$^R$, Tet$^S$), and constituted the desired *E. coli* K12 HB101/pLR2 transformants.

Representative plasmids and transformants that can be constructed in accordance with the foregoing teaching include the following listed below in Tables 1 and 2.

TABLE 1

Representative Plasmids

| Example No. | Plasmid Name | ~ Size in kb | E. coli Marker | Streptomyces Marker | Construction |
|---|---|---|---|---|---|
| 30 | pJL122 | 24.4 | Amp$^R$, Tet$^R$ | M | SstI Deletion of pJL120 |
| 31 | pJL123 | 27.8 | Amp$^R$, Tet$^R$ | M | BglII Deletion of pJL121 |
| 32 | pJL124 | 21.1–24.2 | Amp$^R$, Tet$^R$ | M | Partial PstI Deletion of pJL120 |
| 33 | pJL126 | 9.1–10.6 | Amp$^R$, Tet$^R$ | M | Partial XorII Deletion of pJL120 |
| 34 | pJL176 | 32.5 | CM$^R$, Tet$^R$ | P* | ~16.6 kb PstI and extraveous ~10.0 kb PstI of SCP2* into PstI Site of pBR325 |
| 35 | pJL1200 | 35.8 | Amp$^R$, Tet$^R$ | M | SCP2 EcoRI Site into pBR325 EcoRI Site |
| 36 | pJL1201 | 35.8 | Amp$^R$, Tet$^R$ | M | Reverse Orientation of pJL1200 |
| 37 | pJL1202 | 24.4 | Amp$^R$, Tet$^R$ | M | SstI Deletion of pJL1200 |
| 38 | pJL1203 | 27.8 | Amp$^R$, Tet$^R$ | M | BglII Deletion of pJL1201 |
| 39 | pJL1204 | 31.1–34.2 | Amp$^R$, Tet$^R$ | M | Partial PstI Deletion of pJL1200 |
| 40 | pJL1205 | 1.02 | Amp$^R$ | M | SalI Deletion of pJL1201 |
| 41 | pJL1206 | 9.1–10.6 | Amp$^R$, Tet$^R$ | M | Partial XorII Deletion of pJL1200 |
| 42 | pJL1706 | 32.5 | CM$^R$, Tet$^R$ | P | ~10.6 kb PstI and extraneous ~10.0 kb PstI of SCP2 into PstI site of pBR325 |
| 43 | pJL1716 | 22.5 | CM$^R$, Tet$^R$ | P | ~16.6 kb PstI of SCP2 into PstI Site of pBR325 |
| 44 | pJL3176 | 22.5 | CM$^R$, Tet$^R$ | P* | ~16.6 PstI of SCP2* into PstI Site of pBR325 |
| 45 | pJL1800 | 12.6 | Amp$^R$, CM$^R$ | P | ~6.0 kb SalI of SCP2 into SalI Site of pBR325 |
| 46 | pJL1801 | 12.6 | Amp$^R$, CM$^R$ | P | Reverse Orientation of pJL1800 |
| 47 | pJL1900 | 25.9 | Amp$^R$ | M, Neo$^R$ | ~19.0 kb EcoRI-HindIII of pJL1201 and ~7.7 kb EcoRI-HindIII of pLR4 |
| 48 | pJL1902 | 25.9 | Amp$^R$ | M, Neo$^R$ | ~19.0 kb EcoRI-HindIII of pJL1201 and ~7.7 kb EcoRI-HindIII of pLR4 |
| 49 | pJL1905 | 12.1 | Amp$^R$ | M, Neo$^R$ | ~5.4 kb EcoRI-SalI of pJL1205 and ~7.5 kb EcoRI-Partial SalI of pLR4 |
| 50 | pJL193 | 6.9 | Amp$^R$ | Thio$^R$ | ~1.35 kb BamHI of pLR2 into BamHI of pBR328 |
| 51 | pJL196 | 12.1 | Amp$^R$ | M, Neo$^R$ | ~5.4 kb EcoRI-SalI of pJL125 into ~7.5 kb EcoRI-partial SalI of pJL192 |
| 52 | pJL197 | 13.1 | Amp$^R$ | M, Neo$^R$, Thio$^R$ | ~1 kb BclI of pJL193 into partial BamHI of pJL196, orientation such that the ClaI site of the ~1 kb BclI fragment is proximal to the SalI site of the pBR322 fragment and such that the SalI site of the ~1 kb BclI site is proximal to the neomycin resistance gene |
| 53 | pJL1907 | 13.1 | Amp$^R$ | M, Neo$^R$, Thio$^R$ | ~1 kb BclI of pJL193 into partial BamHI of pJL1905 |
| 54 | pJL198 | 13.1 | Amp$^R$ | M, Neo$^R$, Thio$^R$ | Same as pJL197 except the orientation of the BclI fragment is reversed |
| 55 | pJL212 | 13.9 | Amp$^R$ | M, Neo$^R$, Thio$^R$ | ~1 kb BclI fragment of pJL193 into partial BamHI of pJL195, orientation and insertion the same as pJL198 |
| 56 | pJL213 | 13.9 | Amp$^R$ | M, Neo$^R$, Thio$^R$ | Same as pHJL212 except the orientation and insertion the same as pJL197 |

TABLE 2

Representative Transformants

1. Streptomyces R/pR$^1$ wherein R is *griseofuscus, ambofaciens, fradiae,* or *lividans* and R$^1$ is independently pJL122, pJL123, pJL124, pJL126, pJL176, pJL1200, pJL1201, pJL1202, pJL1203, pJL1204, pJL1205, pJL1206, pJL1706, pJL1800, pJL1801, pJL1900, pJL1902, pJL1905, pJL196, pJL197, pJL1907, pJL198, pHJL212 and pHJL213.
2. *E. coli* K12 R$^2$/pR$^1$ wherein R$^2$ is C600R$_k$-M$_k$-, 294, C600 or RV308 and R$^1$ is independently as defined above.

We claim:

1. A recombinant DNA cloning vector comprising
   (a) a functional origin of replication-containing DNA segment which corresponds, at least at one end of said segment, to DNA contained within the ~15 kb BamHI-PstI restriction fragment of a plasmid selected from the group consisting of plasmids SCP2 an SCP2* and characterized further in that said segment comprises the ~5.4 kb EcoRI-SalI restriction fragment of a plasmid selected from said group,
   (b) a restriction fragment comprising an *E. coli* origin of replication,
   (c) one or more DNA segments that confer resistance to at least one antibiotic when transformed into a cell of *E. coli*, said cell being sensitive to an antibiotic for which resistance is conferred, and
   (d) one or more DNA segments that independently confer either or both of the Streptomyces tra function or resistance to at least one antibiotic when transformed into a cell of Streptomyces, said cell being sensitive to the antibiotic for which resistance is conferred.

2. The cloning vector of claim 1 which is a plasmid.

3. The cloning vector of claim 2 wherein the restriction fragment of plasmid SCP2 or SCP2* is selected from the group consisting of the ~5.4 kb EcoRI-SalI fragment, ~6.0 kb SalI fragment, ~19 kb EcoRI-HindIII fragment, and ~31 kb EcoRI fragment and wherein the E. coli origin of replication is selected from the group consisting of the pBR322 origin of replication, pBR324 origin of replication, pBR325 of replication, pBR327 origin of replication, and pBR328 origin of replication, and wherein the one or more DNA segments that confer resistance in E. coli are selected from the group consisting of DNA segments that confer resistance to ampicillin, chloramphenicol and tetracycline and wherein the one or more DNA segments that confer resistance in Streptomyces are selected from the group consisting of DNA segments that confer resistance to neomycin and thiostrepton.

4. The cloning vector of claim 3 which comprises the ~5.4 kb EcoRI-SalI fragment of plasmid SCP2 or SCP2*, the pBR325 origin of replication, and DNA segments that confer resistance to neomycin and ampicillin.

5. The cloning vector of claim 2 wherein the one or more DNA segments that confer resistance in E. coli are selected from the group consisting of DNA segments that confer resistance to ampicillin, chloramphenicol and tetracycline and wherein the one or more DNA segments that confer resistance in Streptomyces are selected from the group consisting of DNA segments that confer resistance to neomycin and thiostrepton.

6. A plasmid selected from the group consisting of plasmid pJL120, pJL121, pJL180, pJL181, pJL125, pJL190, pJL192, pJL195, pJL199, pJL122, pJL123, pJL124, pJL1200, pJL1201, pJL1202, pJL1203, pJL1204, pJL1205, pJL1800, pJL1801, pJL1900, pJL1902, pJL1905, pJL193, pJL196, pJL197, and pJL1907.

7. The plasmid of claim 6 which is pJL197.
8. The plasmid of claim 6 which is pJL121.
9. The plasmid of claim 6 which is pJL180.
10. The plasmid of claim 6 which is pJL181.
11. The plasmid of claim 6 which is pJL125.
12. The plasmid of claim 6 which is pJL190.
13. The plasmid of claim 6 which is pJL192.
14. The plasmid of claim 6 which is pJL195.
15. The plasmid of claim 6 which is pJL199.
16. The plasmid of claim 2 which is plasmid pJL198.
17. The plasmid of claim 6 which is pJL1200.
18. The plasmid of claim 6 which is pJL1205.
19. The plasmid of claim 6 which is pJL1800.
20. The plasmid of claim 6 which is pJL1900.
21. The plasmid of claim 6 which is pJL1902.
22. The plasmid of claim 6 which is pJL1905.
23. The plasmid of claim 6 which is pJL120.
24. The plasmid of claim 6 which is pJL196.
25. The plasmid of claim 6 which is pJL1907.

26. The cloning vector of claim 1 wherein the DNA segment that confers resistance to an antibiotic is selected from the group consisting of the ~7.7 kb EcoRI-HindIII restriction fragment of plasmid pJL192, 7.7 kb EcoRI-HindIII restriction fragment of plasmid pLR4, the ~7.5 kb EcoRI-Partial SalI restriction fragment of plasmid pLR4, the ~1.35 kb BamHI restriction fragment of plasmid pLR2, and the ~1kb BclI restriction fragment of plasmid pJL193.

27. The cloning vecot of claim 1 which is a plasmid pJL190 or pJL195 high resistance mutant that in Streptomyces confers resistance to neomycin at levels of at least 10 μg/ml.

28. A transformed host cell comprising a cloning vector of claim 1.

29. The transformed host cell of claim 28 which is Streptomyces.

30. The transformed host cell of claim 28 which is E. coli K12.

31. The transformed host cell of claim 29 wherein the Streptomyces is selected from the group consisting of Streptomyces lividans, Streptomyces griseofuscus, Streptomyces fradiae, and Streptomyces ambofaciens.

32. The transfomed host cell of claim 29 which is Streptomyces griseofuscus/pHJL212.

33. The transformed host cell of claim 29 which is Streptomyces lividans/pHJ212.

34. The transformed host cell of claim 29 which is Streptomyces fradiae/pHJL212.

35. The plasmid of claim 2 which is plasmid pHJ212.

36. A transformed host cell comprising a plasmid selected from the group consisting of pJL120, pJL121, pJL180, pJL181, pJL125, pJL190, pJL192, pJL195, pJL199, pJL122, pJL123, pJL124, pJL1200, pJL1201, pJL1202, pJL1203, pJL1204, pJL1205, pJL1800, pJL1801, pJL1900, pJL1902, pJL1905, pJL193, pJL196, pJL197, and pJL1907.

37. The transformed host cell of claim 36 which is E. coli K12.

38. The transformed host cell of claim 36 which is Streptomyces.

39. The transformed host cell of claim 38 which is selected from the group consisting of Streptomyces lividans, Streptomyces griseofuscus, Streptomyces fradiae, and Streptomyces ambofaciens.

40. The transformed host cell of claim 39 which is Streptomyces fradiae/pJL181.

41. The transformed host cell of claim 39 which is Streptomyces griseofuscus/pJL190.

42. The transformed host cell of claim 35 which is Streptomyces fradiae/pJL192.

43. The transformed host cell of claim 39 which is Streptomyces lividans/pJL195.

44. The transformed host cell of claim 39 which is Streptomyces lividans/pJL120.

45. The transformed host cell of claim 39 which is Streptomyces griseofuscus/pJL121.

46. The transformed host cell of claim 39 which is Streptomyces griseofuscus/pJL125.

47. The transformed host cell of claim 38 which is Streptomyces lividans/pJL180.

48. The transformed host cell of claim 39 which is Streptomyces lividans/pJL192.

49. The transformed host cell of claim 39 which is Streptomyces fradiae/pJL1905.

50. The transformed host cell of claim 39 which is Streptomyces griseofuscus/pJL197.

51. The isolated DNA fragment consisting of the ~5.4 kb Eco RI-Sal I restriction fragment of a plasmid selected from the group consisting of SCP2 and SCP2*.

52. The isolated DNA fragment consisting of the ~6.0 kb Sal I restriction fragment of a plasmid selected from the group consisting of SCP2 and SCP2*.

53. The isolated DNA fragment consisting of the ~7.7 kb Eco RI-Hind III restriction fragment of plasmid pJL192.

54. A method for detecting transformants comprising:
(1) mixing Streptomyces cells, under transforming conditions, with a recombinant DNA cloning vector, said vector comprising
   (a) an origin of replication and P gene-containing restriction fragment of plasmid SCP2 or SCP2*, and
   (b) a non-lethal DNA sequence cloned into the EcoRI restriction site of said P gene, and
(2) growing said Streptomyces cells on a lawn of an indicator Streptomyces strain and selecting colonies that show the M pock phenotype.

55. The method of claim 54 wherein said origin of replication and P gene-containing restriction fragment are of plasmid SCP2*.

56. The method of claim 55 wherein the Streptomyces cells and indicator strain are *Streptomyces lividans*.

57. The method of claim 54 or 55 wherein the Streptomyces cells and indicator strain are *Streptomyces griseofuscus*.

58. The method of claim 55 wherein the Streptomyces cells and indicator strain are *Streptomyces fradiae*.

59. The method of claim 55 wherein the Streptomyces cells and indicator strain are Streptomyces ambofaciens.

60. The method of claim 55 wherein the recombinant DNA cloning vector is selected from the group consisting of plasmid pJL120, pJL121, pJL125, pJL190, pJL192, and pJL195.

61. The method of claim 55 wherein the recombinant DNA cloning vector is plasmid pJL197.

62. The method of claim 55 wherein the recombinant DNA cloning vector is plasmid pHJL212.

63. The plasmid of claim 2 which is plasmid pHJL213.

* * * * *

UNITED STATES PATENT AND TRADEMARK OFFICE
CERTIFICATE OF CORRECTION

PATENT NO.  : 4,752,574

DATED       : June 21, 1988

INVENTOR(S) : Charles L. Hershberger and Jeffrey L. Larson

It is certified that error appears in the above-identified patent and that said Letters Patent is hereby corrected as shown below:

Column 8, line 15 - "am.aromycin" should be --amaromycin--, and "(anaromycin)" should be --(amaromycin)--

Column 9, lines 8-9 - "mants are preferred. DNA cloning vectors and transfor" should be --DNA cloning vectors and transformants are preferred--

Column 9, line 21 - "pJL180" should be --pJL192--

Column 10, line 28 - "gene Thus" should be --gene. Thus--

Column 10, line 50 - "resistanceconferring" should be --resistance-conferring--

Column 11, line 42 - "conditions a" should be --conditions over a--

Column 12, bottom of page - Footnotes do not have asteriks by them.

Column 13, line 33 - Footnotes do not have asteriks by them.

Column 14, line 14 - Footnote does not have asterik by it.

Column 15, line 29 - "C600$R_k$-$M_k$" should be --C600$R_k$-$M_k$- --

Column 15, line 54 - "were diluted" should be --were then diluted--

Column 16, line 17 - "∿m 6.0kb" should be --∿6.0kb--

Column 16, line 19 - "0.993%" should be --.093%--

UNITED STATES PATENT AND TRADEMARK OFFICE
CERTIFICATE OF CORRECTION

PATENT NO. : 4,752,574

DATED : June 21, 1988

INVENTOR(S) : Charles L. Hershberger and Jeffrey L. Larson

It is certified that error appears in the above-identified patent and that said Letters Patent is hereby corrected as shown below:

Column 16, line 19 - "Na$_2$DETA" should be --Na$_2$EDTA--

Column 16, line 21 - "in a dialysis bag" should be --placed in a dialysis bag--

Column 16, line 21 - "at 100v" should be --at 100 V--

Column 16, line 42 - "60 mM MgCl2" should be --60 mM MgCl$_2$--

Column 18, line 30 - Insert --*-- before first footnote.

Column 18, line 64 - In title "C600R-M-/pJL190" should be --C600R$_k$-M$_k$-/pJL190--

Column 19, line 48 - Delete "DE52/electroelation" (repeated twice)

Column 20, line 14 - "E. coli C600R$_k$-" should be --E. coli K12 C600R$_k$--

Column 20, line 35 - Delete "30"

Column 20, line 39 - "MgClhd 2" should be --MgCl$_2$--

Column 20, line 50 - In title, delete "=" sign.

Column 24, Seven (7) places in Section B, "µ•" should be --µl--

Column 24, Seven (7) places in Section C, "µ" should be --µl--

Column 24, lines 49 and 51, "µ" should be --µl--

UNITED STATES PATENT AND TRADEMARK OFFICE
CERTIFICATE OF CORRECTION

PATENT NO. : 4,752,574

DATED : June 21, 1988

INVENTOR(S) : Charles L. Hershberger and Jeffrey L. Larson

It is certified that error appears in the above-identified patent and that said Letters Patent is hereby corrected as shown below:

Column 25, Example No. 39, in column 3 of Table 1 - "31.1-34.2" should be --21.1-24.2--

Column 25, Example No. 40, in column 3 of Table 1 - "1.02" should be --10.2--

Column 27, Claim 3, line 8 - "pBR325 of replication" should be --pBR325 origin of replication--

Column 27, Claim 26, line 4 - "pJL192, 7.7 kb" should be --pJL192, the 7.7 kb--

Column 28, Claim 33, line 2 - "pHJ212" should be --pHJL212--

Column 28, Claim 35, line 1 - "pHJ212" should be --pHJL212--

Column 28, Claim 42, line 1 - "35" should be --39--

Signed and Sealed this

Third Day of March, 1992

Attest:

HARRY F. MANBECK, JR.

Attesting Officer     Commissioner of Patents and Trademarks